US012778631B2

(12) United States Patent
Coppedge et al.

(10) Patent No.: US 12,778,631 B2
(45) Date of Patent: Nov. 3, 2026

(54) INTRAOSSEOUS ACCESS DEVICE

(71) Applicant: Trio Medical Corporation, Memphis, TN (US)

(72) Inventors: Billie Coppedge, Branson, MO (US); Andrew Dickson, Knoxville, TN (US); Lawrence Kluge, Long Grove, IL (US); Evgeniya Moiseeva, Louisville, KY (US); Isabella Lindquist, Louisville, KY (US); William Brent White, Charlestown, IN (US); Vas Abramov, Louisville, KY (US)

(73) Assignee: Trio Medical Corporation, Memphis, TN (US)

( * ) Notice: Subject to any disclaimer, the term of this patent is extended or adjusted under 35 U.S.C. 154(b) by 0 days.

(21) Appl. No.: 19/176,532

(22) Filed: Apr. 11, 2025

(65) Prior Publication Data

US 2026/0060717 A1 Mar. 5, 2026

Related U.S. Application Data

(60) Provisional application No. 63/668,762, filed on Jul. 8, 2024, provisional application No. 63/633,314, filed on Apr. 12, 2024.

(51) Int. Cl.

| | |
|---|---|
| ***A61B 17/16*** | (2006.01) |
| ***A61B 17/34*** | (2006.01) |
| *A61B 17/00* | (2006.01) |

(52) U.S. Cl.

CPC ...... *A61B 17/3472* (2013.01); *A61B 17/3476* (2013.01); *A61B 2017/00424* (2013.01)

(58) Field of Classification Search

CPC ............ A61B 17/1622; A61B 17/3476; A61B 17/3472

See application file for complete search history.

(56) References Cited

U.S. PATENT DOCUMENTS

| | | | |
|---|---|---|---|
| 2005/0131345 A1 | 6/2005 | Miller | |
| 2011/0028976 A1 | 2/2011 | Miller | |
| 2020/0297382 A1* | 9/2020 | Coppedge .......... | A61B 17/3472 |
| 2021/0093357 A1 | 4/2021 | Pett et al. | |
| 2022/0304705 A1 | 9/2022 | Coppedge et al. | |
| 2023/0157725 A1 | 5/2023 | Morgan et al. | |

OTHER PUBLICATIONS

PCT International Search Report and Written Opinion, Application No. PCT/US2025/024246, dated Jun. 4, 2025.

* cited by examiner

*Primary Examiner* — Samuel S Hanna

(74) *Attorney, Agent, or Firm* — MacMillan, Sobanski & Todd, LLC

(57) ABSTRACT

The disclosure relates to an intraosseous access device comprising a barrel, a motor, a slide carrier, a rotating stylet assembly, and a handle. The rotating stylet assembly is actuated through the barrel with the slide carrier and rotated by the motor. Elements of the rotating stylet assembly may rotate through the cortex of a bone. The drill may also comprise a shield disposed within the barrel, a slide interface both disposed within a slide channel and attached to the slide carrier, a spring disposed within the barrel, and a removable pivot body attached to both the handle and the barrel.

19 Claims, 26 Drawing Sheets

INTRAOSSEOUS ACCESS DEVICE

FIELD

The disclosure relates generally to the field of medical devices. More particularly, the disclosure relates to intraosseous access devices, such as drills, useful in establishing access to the medullary space within a bone of an animal, such as a human being.

BACKGROUND intraosseous access device Intraosseous procedures provide a means of accessing the medullary space of a bone, often as an alternative to intravenous access when rapid delivery of fluids, medications, or other therapeutic agents is required. IO access is commonly used in emergency and critical care settings, but is also increasingly being employed in elective and post-operative contexts. In addition to providing a route for acute medication delivery, intraosseous techniques are used to obtain bone marrow samples for diagnostic biopsy procedures and to implant ports or other devices for repeated or long-term delivery of therapeutic agents directly into the intraosseous space.

Devices used for intraosseous access—such as handheld drills or powered insertion tools—typically include components such as stylets, needles, or other penetrating elements designed to breach the hard cortical layer of bone. These components often have sharp, tapered, or rotating ends to facilitate penetration, which may pose a safety hazard to clinicians or other users during setup, use, or disposal. Although some conventional intraosseous devices incorporate safety features intended to reduce the likelihood of accidental contact or exposure to sharp components, risks of user injury remain. In particular, injury may occur when handling the device before or after insertion, or if the protective measures fail or are inadvertently bypassed during operation.

A need therefore exists for improved intraosseous access devices, such as intraosseous access devices.

BRIEF SUMMARY OF SELECTED EXAMPLES

Various example intraosseous access devices are described.

An example intraosseous access device comprises a barrel, a motor, a slide carrier, a rotating stylet assembly, a handle, and a shield disposed within the barrel.

Another example intraosseous access device comprises a barrel, a motor, a slide carrier, a rotating stylet assembly, a handle, and a slide interface both disposed within a slide channel and attached to a slide carrier.

Another example intraosseous access device comprises a barrel, a motor, a slide carrier, a rotating stylet assembly, a handle, and a spring disposed within the barrel.

Another example intraosseous access device comprises a barrel, a motor, a slide carrier, a rotating stylet assembly, a handle, and a removable pivot body attached to both the handle and the barrel.

Another example intraosseous access device comprises a barrel, a motor, a slide carrier, a rotating stylet assembly, a handle, and release collar disposed within the barrel.

Another example intraosseous access device comprises a barrel, a motor, a slide carrier, a rotating stylet assembly, a handle, and a latch attached to the slide interface.

Another example intraosseous access device comprises a barrel, a motor, a slide carrier, a rotating stylet assembly, a handle, and a clutch able to be engaged to actuate with the motor.

Additional understanding of these examples and other intraosseous access devices, components of intraosseous access devices, and methods of using intraosseous access devices in various procedures, such as establishing access to an intramedullary space, delivery of medicine to a location in a body, such as an intramedullary space, and obtaining of biopsy or other tissue samples from a body, can be obtained by review of the detailed description of selected examples, below, and the figures.

DETAILED DESCRIPTION OF SELECTED EXAMPLES

The following detailed description and the appended drawings describe and illustrate various example intraosseous access devices. The description and illustration of these examples are provided to enable one skilled in the art to make and use intraosseous access devices, such as drills. The inclusion of detailed descriptions of these examples is not intended to limit the scope of the invention, or its protection, in any manner. The invention is capable of being practiced or carried out in various ways and the examples described and illustrated herein are not considered exhaustive.

Figure 1:
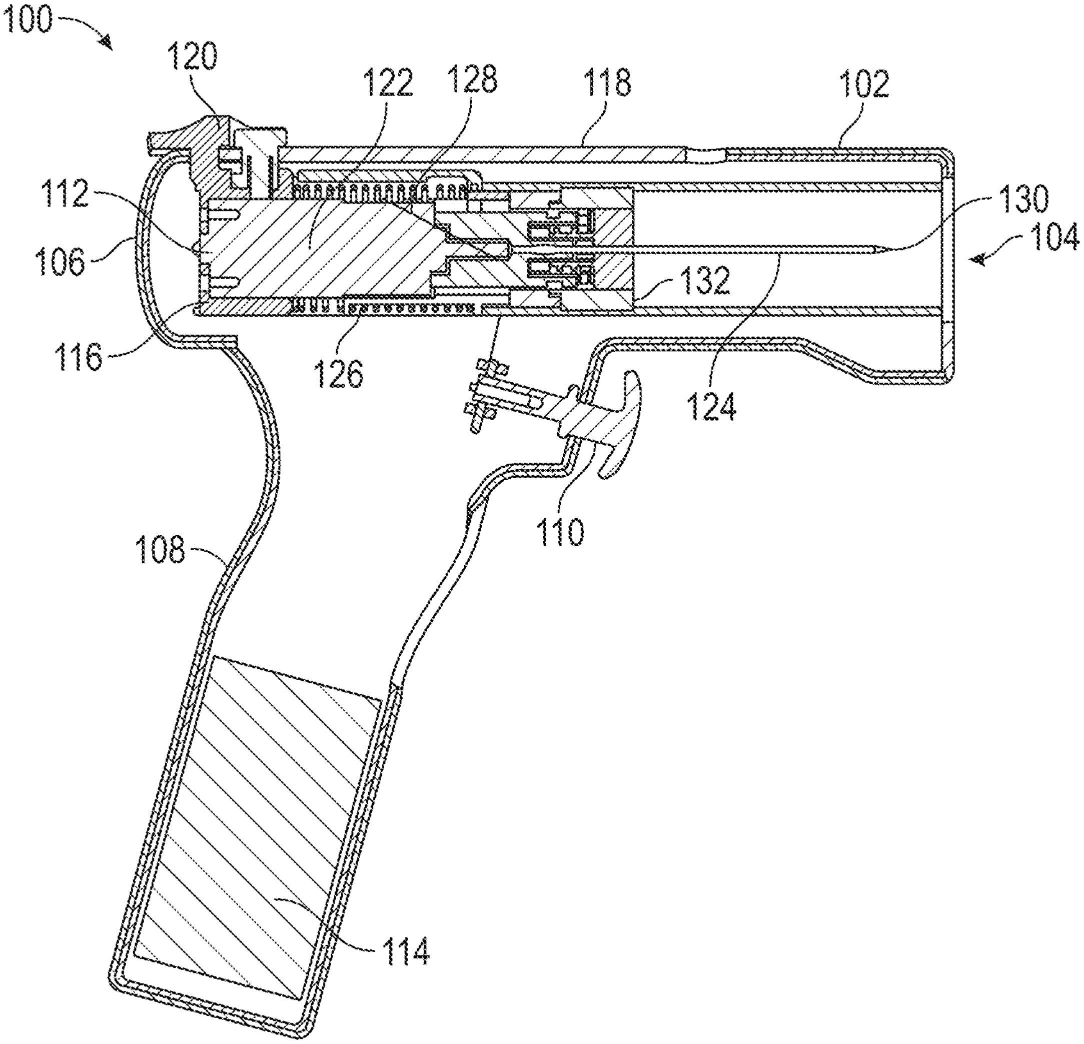
FIG. 1 illustrates an example intraosseous access device.

FIG. 1 illustrates an intraosseous access device 100. The intraosseous access device 100 may include a barrel 102. The barrel 102 may include a closed end 106 and an open end 104. The closed end 106 may be disposed proximal to a user when operating the intraosseous access device, while the open end 104 may be disposed distal to a user when operating the intraosseous access device. The intraosseous access device may include a slide carrier 116. The slide carrier 116 may be attached to the motor 112. The slide carrier 116 may be configured to actuate throughout the barrel 102. As such, the slide carrier 116 may be configured to actuate the motor 112 throughout the barrel 112. The slide carrier 116 is configured to actuate between the proximal end of the intraosseous access device and the distal end of the intraosseous access device. Even further, the slide carrier 116 is allowed to actuate relatively parallel to the barrel 102. The barrel 102 is configured to include a slide channel 118. The slide channel 118 defines the path for the slide interface 120. The slide interface 120 is adjacent to the barrel 102 and disposed within the slide channel 118. The slide interface 120 may allow manual actuation of the slide carrier 116, and any attached components, throughout the barrel 102. This slide carrier 116 is attached to other components allowing for their actuation within the barrel 102 and potentially through the open end 104 of the barrel 102. These other components may include a rotating stylet assembly 122, a motor 112, and a slide interface 120.

The motor 112 may be configured to provide torque and speed required for drilling into bone tissue. The motor 112 may be disposed in the barrel 102. The motor 112 may be configured to be powered by a variety of energy sources. The motor 112 within an intraosseous access device is configured to allow a user control over the drilling process. This may enable the user to operate the intraosseous access device upon bone tissue with lower effort, thus increasing the accuracy of the operation. The choice of motor 112 may be tailored to specific use-case requirements such as portability, power output, and operational environment. In one example, the motor 112 may be configured to be powered by an electrical power source. In another example, the motor may be configured to be powered by a compressed gas power source.

In embodiments in which the motor 112 is configured to be electrically driven, the motor 112 may be configured to operate on AC power. This embodiment of motor 112 may also be fitted with inversion capabilities such that they are configured to be attached to an electrical power source providing DC power. Other embodiments of the motor 112 may be configured to operate on DC power. As such, the motor may be configured to receive power directly from a DC power source such as a power supply or a battery. This embodiment of motor 112 may also be fitted with rectifying capabilities such that they are configured to be attached to an electrical power source providing AC power.

In some embodiments, a pneumatic motor is used, such as an air-driven motor. In these embodiments, the motor 112 is configured to be driven by compressed gas temporarily stored within the intraosseous access device 100. For example, the motor 112 may be configured to be powered by compressed gas stored within a cartridge that is removably or permanently disposed within the body of the intraosseous access device 100, such as within the handle 108. The charged cartridge may be configured to hold compressed gas, such as compressed CO2, compressed air, or another compressed gas. In these embodiments, the handle assembly is configured to accept a cartridge containing the compressed gas. The inventors have determined that a CO2 cartridge of 16 g or larger is suitable for these embodiments. Alternatively, multiple cartridges of compressed gas can be used. Also in these embodiments, the intraosseous access device includes an air motor, valve switch, and appropriate gas supply lines, such as tubing, to allow for selective engagement of the motor by the compressed gas. An air motor having a gearbox providing a maximum of 2500 revolutions per minute at between about 60-120 PSI of the compressed gas is considered advantageous. Intraosseous access devices according to these embodiments advantageously also include a pressure or flow control mechanism to regulate revolutions per minute. For example, a regulator that caps revolutions per minute at 1500 is considered advantageous. In some embodiments, the motor 112 may be configured to receive power from a local pneumatic power source including local pneumatic pumps. In these embodiments, the intraosseous access device 100 may be configured to receive a hose attached to the pneumatic power source. Also alternatively, torsion, coil, or other springs can be incorporated an used to drive rotation of the needle.

The rotating stylet assembly 122 is attached to and powered by the motor 112.

A button assembly 206 is positioned on the barrel 102 and disposed within the slide channel 118. The button assembly 206 may enable actuation of the slide interface 120 within the slide channel 118, disable actuation of the slide interface 120 within the slide channel 118, and activate the decompression of a spring 126. The spring 126 within an intraosseous access device may be configured to assist in controlled retraction of the stylet assembly 122. The spring 126 may be configured to be disposed within the barrel 102 of the intraosseous access device.

The spring 126 is configured to store mechanical energy when compressed. In some embodiments, the spring 126 is configured to retract the stylet 126 when the spring 126 is released. The retractable stylet 124 may be a safety position for the intraosseous access device. In other embodiments, the spring 126 may be configured to actuate the stylet 124 towards a point of operation, or extend the stylet 124 towards bone tissue. The material composition of spring 126, may be tailored to specific use-case requirements. For example, in an embodiment having high repetitive use, the spring 126 may be composed of a material that is resistant to ware. In other embodiments, the spring 126 may be configured to be biocompatible.

Upon decompression the spring 126 will engage in a retraction of the slide carrier 116 toward the closed end 106 of the barrel 102. The attachment of the slide carrier 116 to other internal components ensures a retraction of attached components toward the closed end 106 of the barrel 102. The spring 126 is an independent component from the slide interface 120, the shield 128, the pivot body 200, the release collar 3202, the clutch 3204, and the latch 3206. Each of the seven components is optional but the intraosseous access device 100 must have at least one.

Figure 2:
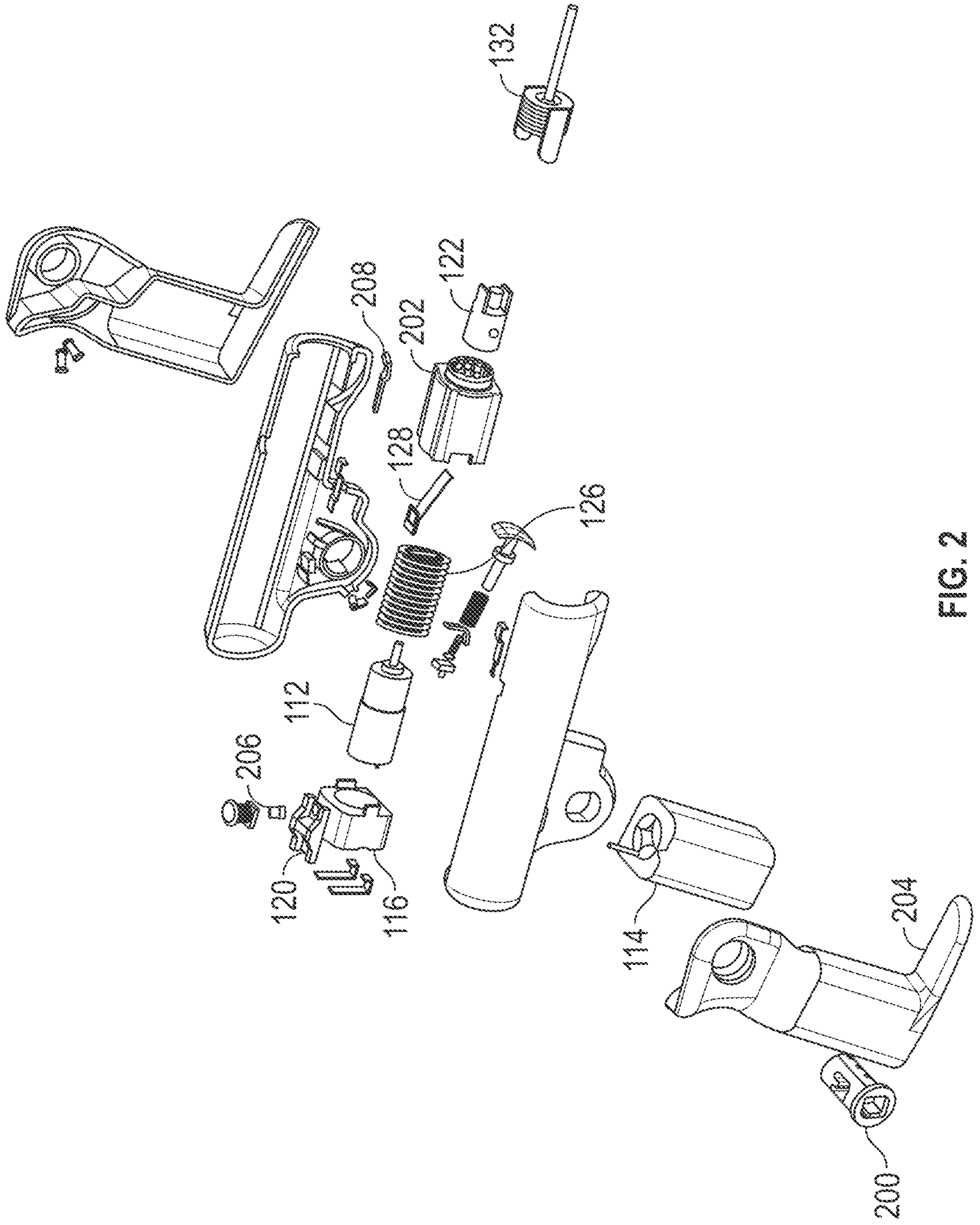
FIG. 2 is an exploded view of an example intraosseous access device.

FIG. 2 illustrates an exploded view of the intraosseous access device 100. The drill 100 features a handle 108 that is attachable to a barrel 102. The attachment of the handle 108 enables the drill 100 to transition between a disabled state in a first pivot position 302 and an enabled state in a second pivot position 402. The drill 100 may lock in the enabled state. The locking may be done automatically when the drill 100 has transitioned from the disabled state to the enabled state. This feature introduces an additional layer of safety, preventing unintended operation of the intraosseous access device 100. A ledge 204 defined by the handle 108 covers the open end 104 of the barrel 102 when in the disabled state, further preventing accidental actuation of the rotating stylet assembly 122. The attachment of the handle 108 to the barrel 102 is achieved through a pivot body 200. The pivot body 200 may be removable in its attachment of the handle 108 to the barrel 102. In one embodiment, the pivot body 200 may be configured to be placed in and used to close the open end 104 of the barrel 102. In such an embodiment, the pivot body 200 is sized according to the open end 104 of the barrel 102. This may allow for the prevention of components actuating through the open end 104 of the barrel 102.

The handle 108 may be equipped with a trigger 110. The trigger 110 may be configured to be actuated between a first released position and a second actuated position. The trigger 110 may be configured to be actuated by a user holding the handle 108. The trigger 110 may be configured to activate the motor 112. In particular, the trigger 110 is configured to send a signal to the motor 112 to activate. Actuation of the trigger 110 by a user is configured to send the signal. Further, the amount of actuation of the trigger 110 may affect the signal sent from the trigger 110 to the motor 112. For example, actuation of the trigger 110 may signal the motor 112 to operate at a corresponding rotational speed that is partial the maximum speed of the motor 112, while full actuation of the trigger 110 may signal the motor 112 to operate at the maximum speed of the motor 112. The maximum speed of the motor may be a predetermined value dependent upon the operation, motor, drill location, etc. The trigger 110 may also be disposed in the barrel 102. Within the handle 108, a power source is housed. A battery 114 serves as the power source for the motor 112.

A shield 128 is positioned within the barrel 102. This shield 128 is capable of transitioning between an open state 1502 that permits the actuation of the rotating stylet assembly 122 and a closed state 1602 that prevents actuation of the rotating stylet assembly 122. One intended use of the shield 128 is to protect the operator from moving parts. Further, the shield 128 may protect the accuracy of the operation itself. For example, if an operator is complete with the operation, the shield 128 may prevent re-actuation of the style 126 beyond the intended depth. While the stylet assembly 122 may be configured to actuate throughout the barrel 102, the shield 128 may be configured to remain static within the barrel 102. The static position of the shield 128 may be relative to the open end of the barrel 102. As such, when the stylet assembly 122 is actuated throughout the barrel 102, the stylet assembly 122 may also be actuated relative to and throughout the shield 128. The shield 128 may be configured with a lip 1002 and a shield aperture 1402. The dimensions of the shield aperture 1402 may correspond to a tapered end 130 of a stylet 124 included on the rotating stylet assembly 122. The corresponding dimensions ensure that the rotating stylet assembly 122 is secure when the shield 128 is in the closed state 1602 and the stylet 124 is contacting the shield 128. The shield 128 forms part of a shield container 202. The shield container 202 may be attached to the open end 104 of the barrel 102. The shield container 202 may feature a container aperture 1202 allowing the shield 128 to move between the open state 1502 and the closed state 1602 in response to the retraction of the rotating stylet assembly 122. This movement of the shield 128 ensures that the drill 100 can transition smoothly into a safe state.

The rotating stylet assembly 122 may include a stylet 124. The stylet 124 within an intraosseous access device may be used for penetration into the bone tissue. The stylet 124 may further be used to guide the drill bit during the drilling process. The stylet 124 may be configured to be both sturdy enough to pierce the outer cortex of a bone while being flexible enough to prevent shattering during an operation. The intraosseous access device may be configured to operate a variety of types of stylets. The choice of stylet 124 may be tailored to specific use-case requirements such as the density of the bone tissue, the intended depth of penetration, and the operational environment of the bone tissue. In one embodiment, the stylet 124 may be configured with a tapered end 130. The tapered end 130 may be used to decrease the difficulty involved with penetrating into the bone tissue. This configuration may allow the stylet 124 to create a pilot hole that further guides the stylet 124. This configuration further reduces the force required for penetration.

The stylet 124 may be composed from materials selected for their strength, durability, and biocompatibility. Examples of materials that the stylet 124 may be composed of are stainless steel or titanium alloys. Other embodiments of the stylet 124 may be configured with materials or coatings that are resistant to corrosion, wear, and thermal expansion. These embodiments may be used in environments with variable temperatures or conditions that may affect material integrity. Additionally, the stylet 124 may be configured for single-use or to be sterilizable for multiple uses, depending on the application requirements. Single-use stylet 124 may be designed with cost-effective materials and disposable after one procedure, ensuring sterility and reducing the risk of cross-contamination. Reusable stylets may be composed of materials for easy sterilization and durability over multiple uses.

The stylet 124 may be configured to be rotated by the motor 112. The stylet 124 may be configured to rotate through the cortex of bone tissue. This rotating stylet assembly 122 is powered by the motor 112. The actuation of the rotating stylet assembly 122 within the barrel 102 is enabled by manual movement of the slide interface 120. The slide interface 120 is an independent component from the spring 126, the shield 128, the pivot body 200, the release collar 3202, the clutch 3204, and the latch 3206. Each of the seven components is optional, but the intraosseous access device 100 must have at least one.

The spring 126 located within the barrel 102 retracts the rotating stylet assembly 122 which is attached to the slide carrier 116. This retraction mechanism may be activated by the button assembly 206. In one embodiment, the retraction may be activated by actuating the button assembly 206 while the rotating stylet assembly 122 is simultaneously rotating. This retraction mechanism may be activated upon reaching a predetermined threshold. Retraction by the spring 126 ensures a swift withdrawal of the stylet 124 after having rotated through the cortex of bone tissue, enhancing the safety and usability of the drill 100.

Figure 3:
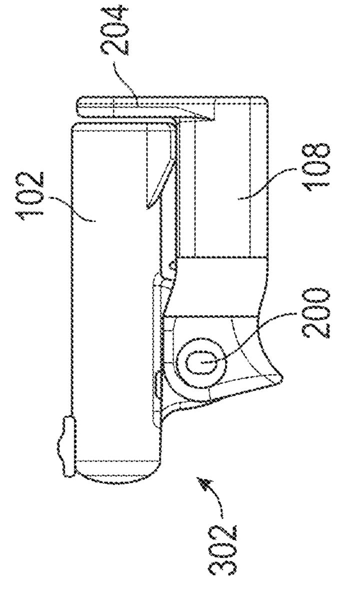
FIG. 3 illustrates an example intraosseous access device in a folded or deactivated configuration.

FIG. 3 illustrates the intraosseous access device 100 configured in a disabled state. The disabled state shows one reason that the drill 100 may be packaged and provided to a customer as able to conduct a procedure. Further, the disabled state may allow a power source to be disconnected. The handle 108 may include a ledge 204. When the handle 108 is positioned in its first pivot position 302, the drill 100 is in the disabled state. As shown, in the disabled state, the handle 108 may be disposed generally parallel to the barrel 102. This reduces the volume required to store the drill 100. In this disabled state the handle 108, in particular, the ledge 204 of the handle 108, covers the open end 104 of the barrel 102. The intraosseous access device 100 may be boxed, shipped, or carried in this state.

The ledge 204 may be configured to be generally perpendicular to the handle 108 in the disabled state. This may allow the ledge 204 to act as a physical barrier that covers the open end 104 of the barrel 102. This coverage is a safety mechanism, as it blocks access to the operational components of the drill 100, such that the rotating stylet assembly 122, nor components contained within, may not be unintentionally actuated through the open end 104 of the barrel 102. Similarly, the disabled state of the intraosseous access device 100, enabled by the positioning of the handle 108 and the ledge 204, ensures that the rotating stylet assembly 122 remains internal until intentionally activated by the user.

Figure 4:
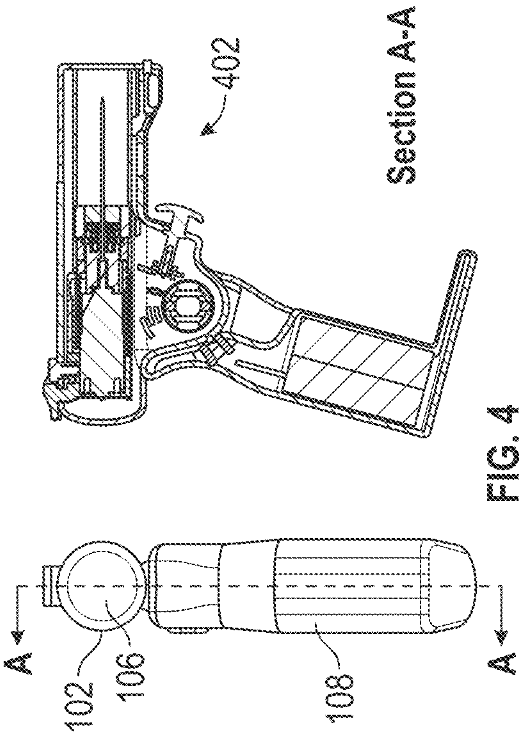
FIG. 4 illustrates an intraosseous access device in an unfolded or activated configuration with a slide carrier in a retracted position and a spring in a compressed state.

FIG. 4 illustrates an intraosseous access device 100 in the enabled state. Further, the drill 100 is shown in a first enabled phase. In this first enabled phase, the handle 108 is positioned in a second pivot position 402, typically at a generally perpendicular angle to the barrel 102. The perpendicular position of the handle 108 relative to the barrel 102 ensures that the user can apply necessary force. To attain the first enabled state from the disabled state shown in FIG. 3, the handle 108 may be rotated about the pivot body 200 generally 90 degrees. In the first enabled phase, the spring 126 within the device is in a compressed state. This compression is indicative of the spring 126 being prepared to provide the necessary force for retraction of the stylet 124, depending on the enabled phase that the intraosseous access device 100 is in. Furthermore, the slide interface 120 and the button 206 are both in retracted positions. The retractable slide interface 120 enables the movement of the stylet 124, ensuring that it can be advanced or retracted within the barrel 102.

The handle 108 in the second pivot position 402 and the slide interface 120 in a retracted position, signifies that the device rotating stylet assembly 122 is ready to be actuated towards the open end 104 of the barrel 102. Actuation of the stylet assembly 122 may be executed manually. The position of the slide interface 120 may affect the position of the stylet 124 in relation to the barrel 102. In the first enabled position, the entire rotating stylet assembly 122 is disposed within the barrel 102. This position of the stylet 124 promotes safety while being correctly aligned and ready for actuation into a second phase.

Figure 5:
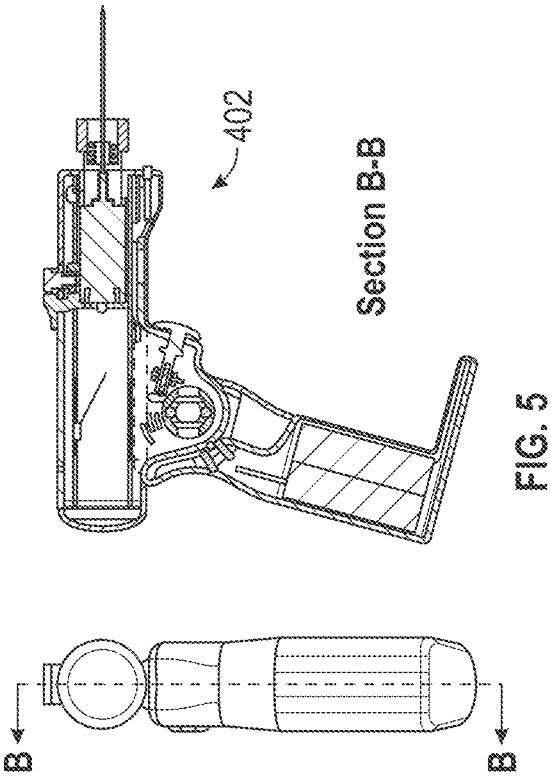
FIG. 5 illustrates an intraosseous access device in an unfolded or activated configuration with a slide carrier in an actuated position and a spring in a compressed state.

FIG. 5 illustrates the intraosseous access device 100 with the slide carrier 116 in an actuated position, showing that the device is ready for operation. In the actuated position, components of the rotating stylet assembly 122 may be partially or entirely external to the barrel 102. The actuated position supports the rotation of the stylet 124 by the motor 112 and into bone tissue while components are partially or entirely external to the barrel 102. The actuation of the slide carrier 116 may allow the device to transition from a first enabled phase to a second enabled phase. The movement of the slide interface 120 may provide the actuation of the slide carrier. The rotating stylet assembly 122 comprises a cannula assembly 132 which is removably attached to the rotating stylet assembly 122. In the second enabled phase, the cannula assembly 132 may be partially inserted into bone tissue.

Figure 6:
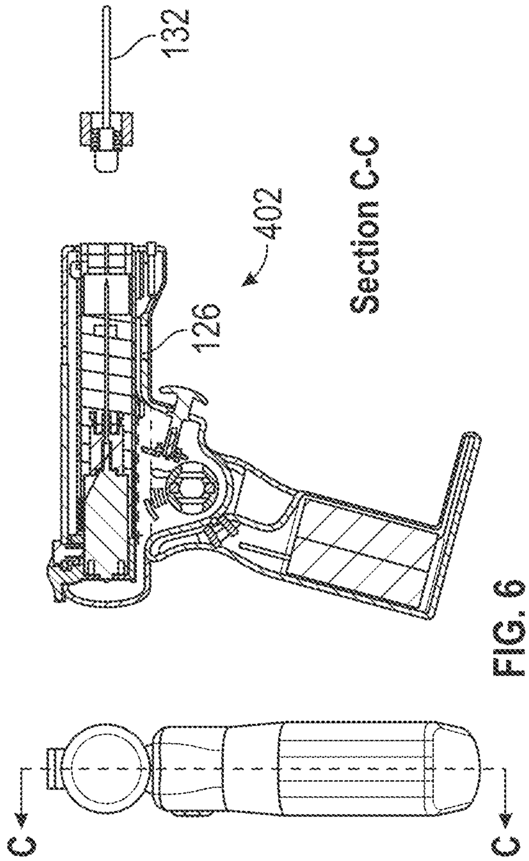
FIG. 6 illustrates an intraosseous access device in an unfolded or activated configuration with a slide carrier in a retracted position and a spring in a decompressed state.

In FIG. 6, the intraosseous access device 100 is illustrated in a third enabled phase. In the third enabled phase, the spring 126 is in a decompressed state. The decompression of the spring 126 may allow components to retract to the closed end 106 of the barrel 102. The cannula assembly 132 is disconnected from the rest of the rotating stylet assembly 122 and is unaffected by the retraction of the spring 126, remaining exterior to the barrel 102. The motor 112, the slide carrier 116, the slide interface 120, and the rotating stylet assembly 122, without the cannula assembly 132, are retracted by the spring 126 towards the closed end 106 of the barrel 102. After disconnecting, the cannula assembly 132 may remain penetrated in the bone tissue.

FIGS. 7 through 16 illustrate shield 128 embodiments. The figures may include top, side, and face views of shield 128 embodiments. The figures illustrate how the shield 128 may secure the stylet 124. This form of safety is active safety as the shield 128 is used to secure the stylet 124. The shield 128 is an independent component from the slide interface 120, the spring 126, the pivot body 200, the release collar 3202, the clutch 3204, and the latch 3206. Each of the seven components is optional, but the intraosseous access device 100 must have at least one.

The shield 128 transitions between an open state 1502 and a closed state 1602 to either expose or secure the tip of the stylet 124 respectively. As a result of securing the tip of the stylet 124, the closed state 1602 of the shield 128 does not allow the slide carrier 116 to actuate enough to release the stylet 124 from the open end 104 of the barrel 102. The shield 128 is in the open state 1502 while the intraosseous access device 100 is in the disabled phase, the first enabled phase, and the second enabled phase. The shield 128 is in the closed state 1602 while the intraosseous access device 100 is in the third enabled phase. The shield 128 may transition from the open state 1502 to the closed state 1602 upon decompression of the spring 126.

The shield 128 may comprise a shield base 1104 and a shield arm 1106. In some embodiments, the shield base 1104 may be separate from the shield arm 1106. In other embodiments, the shield base 1104 may be integral with the shield arm 1106. The shield base 1104 may incorporate a shield support 702 to remain attached to the shield container 202 in the open state 1502 and the closed state 1602. The shield base 1104 and the shield arm 1106 are relatively parallel to the barrel 102 in the open state 1502. The shield base 1104 is relatively parallel to the barrel 102 in the closed state 1602, while the shield arm 1106 is angled relative to the barrel 102 in the closed state 1602.

Figure 8:
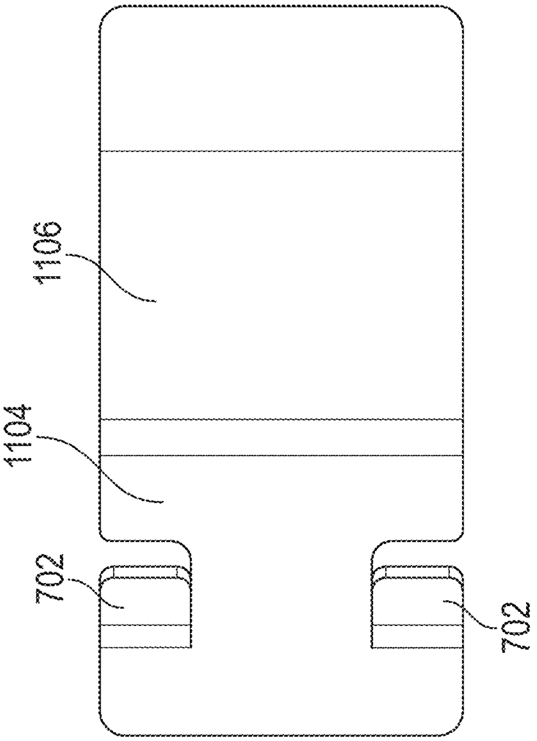
FIG. 8 is a top view of the shield illustrated in FIG. 7.
Figure 9:
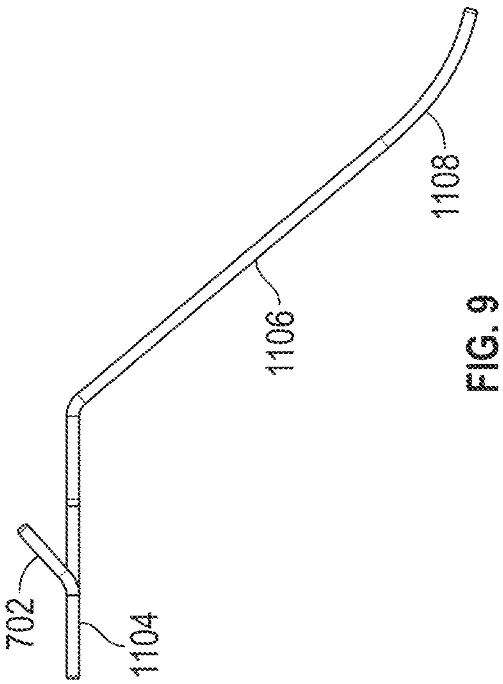
FIG. 9 is a side view of a the shield illustrated in FIG. 7.
Figure 7:
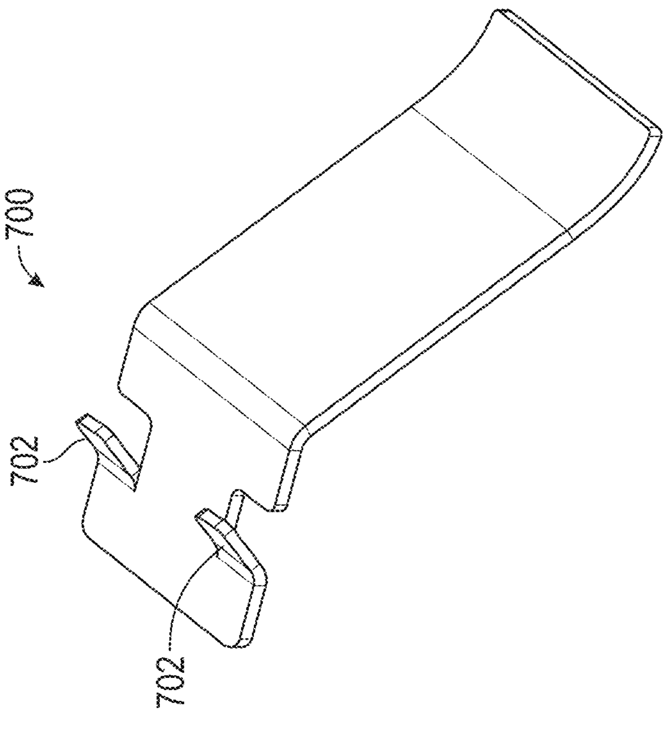
FIG. 7 illustrates a shield suitable for use in an intraosseous access device.

FIGS. 7 through 9 illustrate multiple views of a first shield embodiment 700. FIG. 7 illustrates the first shield embodiment 700 in the closed state 1602. The first shield embodiment 700 may have two shield supports 702 allowing the shield 128 to remain attached to the shield container 202 while transitioning between the open state 1502 and the closed state 1602. The first shield embodiment 700 does not contain a lip 1002 or a shield aperture 1402.

FIGS. 8 through 9 illustrate measurements and angles of the first shield embodiment 700 and the shield supports 702. FIG. 8 illustrates each shield support 702 sharing an outer dimension with the exterior of the shield base 1104. FIG. 9 illustrates a shield arm upward curve 1108 in the shield arm 1106. The shield arm upward curve 1108 is configured to contact the shield arm 1106 with the stylet 124 at a specific location inside the barrel 102. The shield arm upward curve 1108 is configured to contact the shield arm 1106 with the stylet 124 at a specific angle inside the barrel 102.

Figure 10:
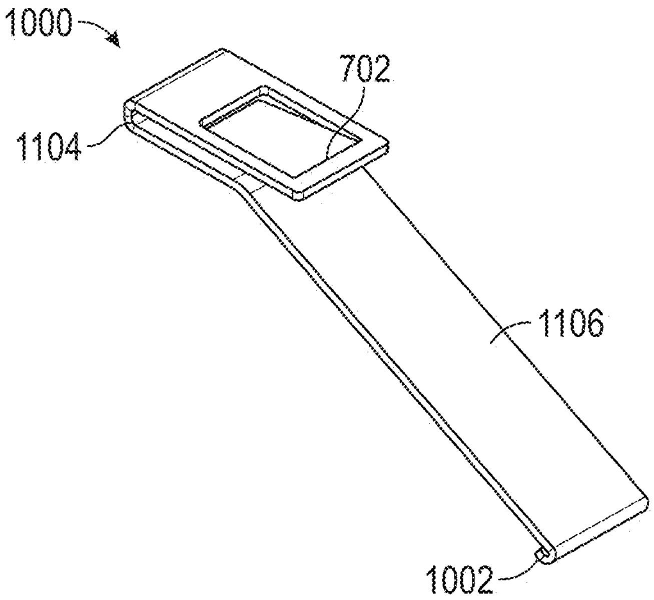
FIG. 10 is a perspective view of a shield suitable for use in an intraosseous access device.
Figure 11:
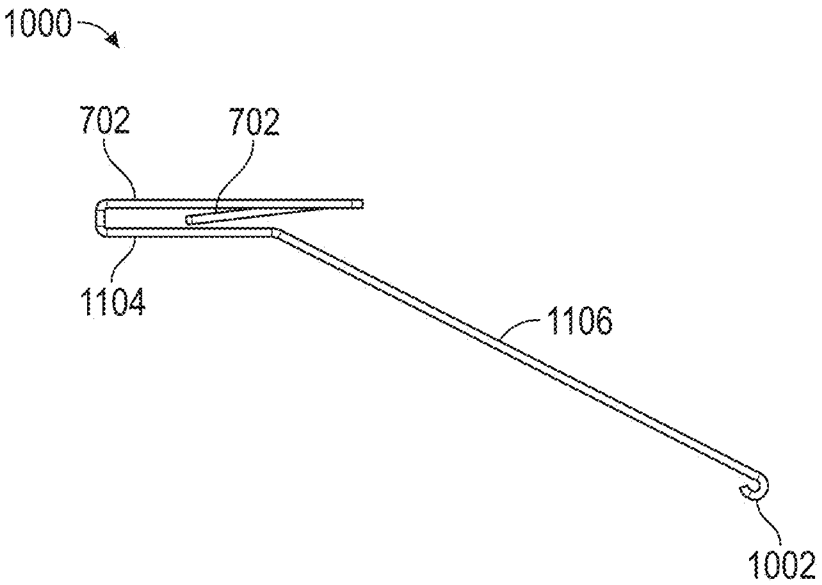
FIG. 11 is a side view of the shield illustrated in FIG. 10.

FIGS. 10 through 11 illustrate multiple views of a second shield embodiment 1000. The second shield embodiment 1000 is shown in the closed state 1602. In this second shield embodiment 1000, the shield 128 has a lip 1002. This second shield embodiment 1000 may not include a shield aperture. Rather a portion of the second embodiment of the shield may act as a clip. This clip portion may be a shield support 702. The shield support 702 may be configured to removably attach to at least one of the shield container and the shield base. FIG. 10 illustrates that the shield support 702 is attached to the shield base 1104 without sharing external dimensions of the shield base 1104. FIG. 11 illustrates that the shield base 1104 of the second shield embodiment 1000 is a configuration including two parallel faces joined at one end.

Figure 12:
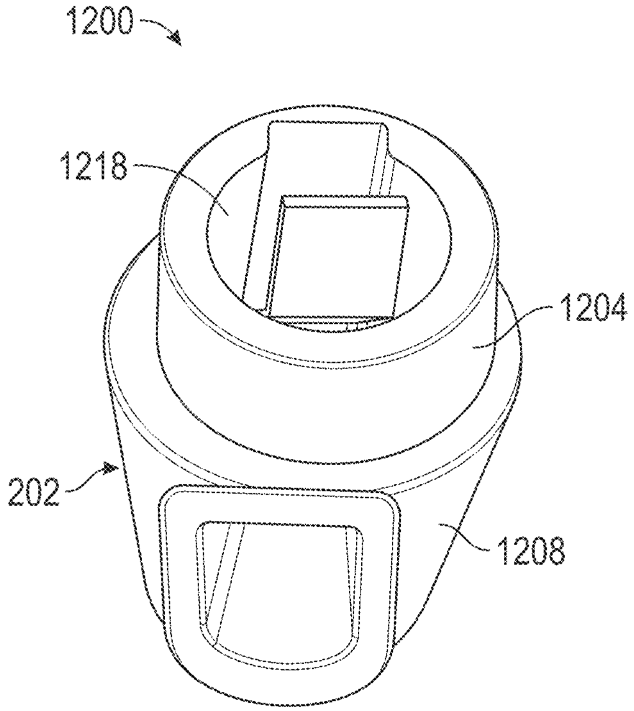
FIG. 12 is a perspective view of a shield container containing a shield in a closed state.
Figure 13:
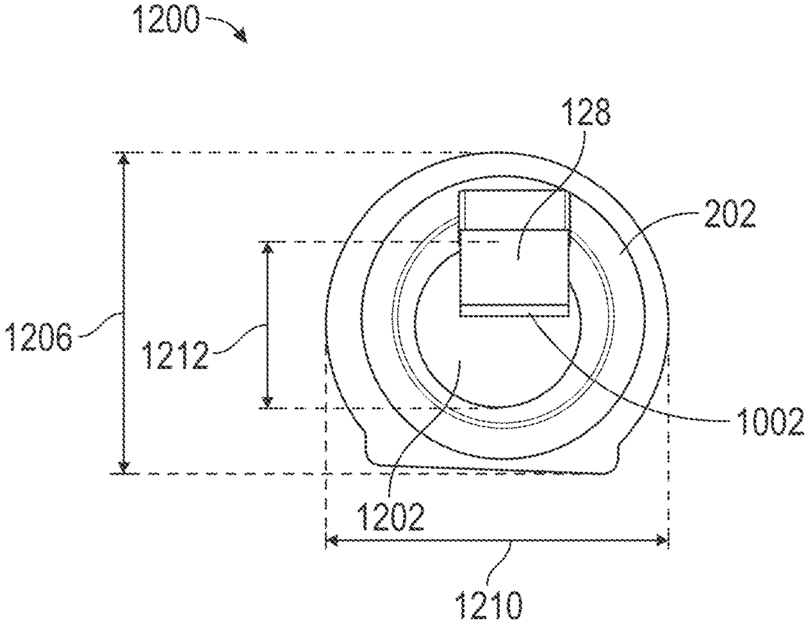
FIG. 13 is a front view of the shield container illustrated in FIG. 12.

FIG. 12 thorough 13 illustrate multiple views of a third shield embodiment 1200. FIG. 12 thorough 13 illustrate the shield 128 in the closed state 1602 inside of the container aperture 1202. While not depicted, the shield 128 may be in an open state in which the stylet 126 is actuate throughout the barrel beyond the shield 128. FIG. 12 illustrates that the shield container 202 may have a first container portion 1204 and a second container portion 1208. The first container portion 1204 may define a first container portion outer surface 1214. The first container portion 1204 may define a first outer container diameter 1206. The second container portion 1208 may define a second outer container diameter 1210. The container aperture 1202 may have an inner container diameter 1212 throughout the first container portion 1204 and the second container portion 1208.

Figure 14:
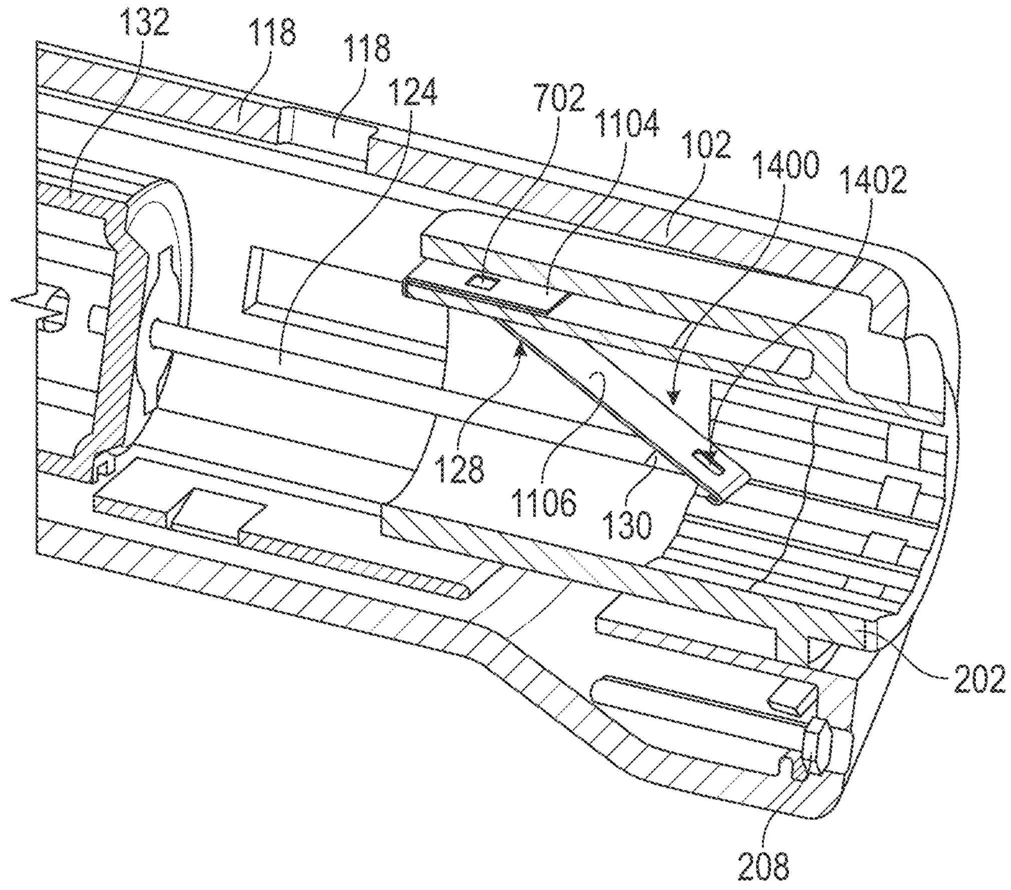
FIG. 14 is a partial sectional view of an open end of a barrel with a stylet in a retracted state and inside of a shield aperture.

FIG. 14 illustrates a cross-sectional view of the open end 104 of the barrel 102 and the shield container 202. Additionally, FIG. 14 illustrates a fourth shield embodiment 1400. As shown, the shield 128 is in the closed state 1602 while it is inside of the container aperture 1202. The fourth shield embodiment 1400 includes the shield 128 with the shield aperture 1402 and the lip 1002. The fourth shield embodiment 1400 shows the shield 128 securing the tip of the stylet 124 within the shield aperture 1402. As shown, the tapered end 130 of the stylet 124 abuts the shield 128, such that the tapered end 130 is disposed partially with the shield aperture 1402. In such a configuration, the surrounding portions of the shield 128 that define the shield aperture 1402 inhibit additional movement of the stylet 124. The shield support 702 is identical to the configuration shown in the second shield embodiment 1000. The shield support 702 is shown to be attached to shield base 1104, and thus the shield container 202. Of note, the shield support 702 attaches to the shield container 202 via a clipping mechanism, in which the clip attaches in the same direction of actuation towards bone tissue. In such a configuration, the stylet 124 is prevented from removing the shield support 702 from the shield container 202. FIG. 14 illustrates an LED assembly 208 configured partially inside of the barrel 102. The LED assembly 208 may have a variety of functions. In one embodiment, the LED assembly 208 may provide light to a user depending on position of the handle 108 in relation to the barrel 102. In one embodiment, the LED assembly 208 may provide light to a user operating the intraosseous access device 100. Additionally, or alternatively, the LED assembly 208 may be configured to provide various colors, indicative of the status of the drill 100. For instance, the LED assembly 208 may alert a user that desired depth has been reached, thus the spring 126 has been released. In another instance, the LED assembly 208 may alert a user that a power source of the drill 100, such as the battery or gas cartridge, is approaching a low energy threshold.

Figure 15:
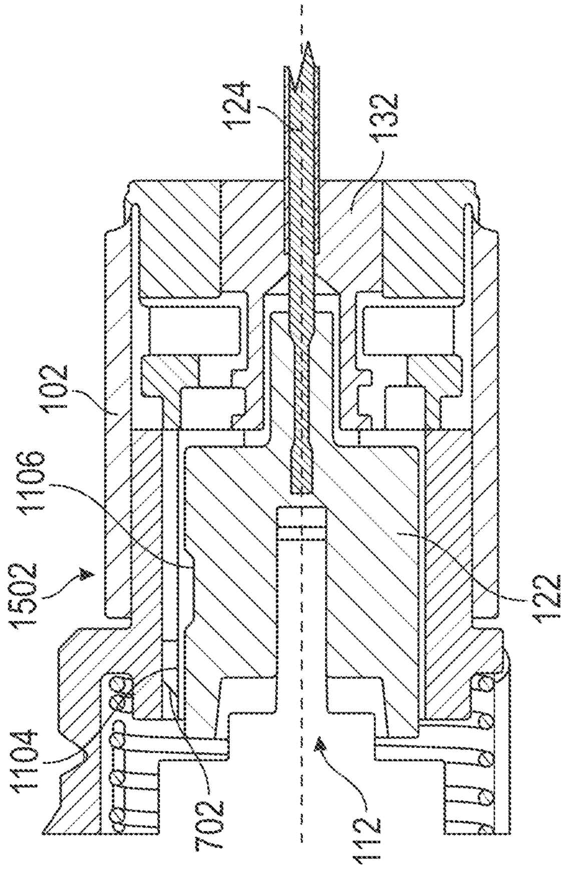
FIG. 15 is a partial sectional view of a barrel, a rotating stylet assembly, and a shield container showing a shield in an open state.

FIG. 15 illustrates the shield 128 in the open state 1502. The shield 128 may be held in the open state 1502 by abutting the stylet assembly 122. As shown, the shield 128 may be attached to the shield container 202. The shield 128 in the open state 1502 may allow for the actuation or retraction of the slide carrier 116. This contrasts the closed state 1602, in which the slide 128 may act inhibit actuation by blocking the path of the slide carrier 116. With a slide carrier 116 that is unblocked, the stylet 124 can be inside the barrel 102 or partially outside of the open end 104 of the barrel 102.

Figure 16:
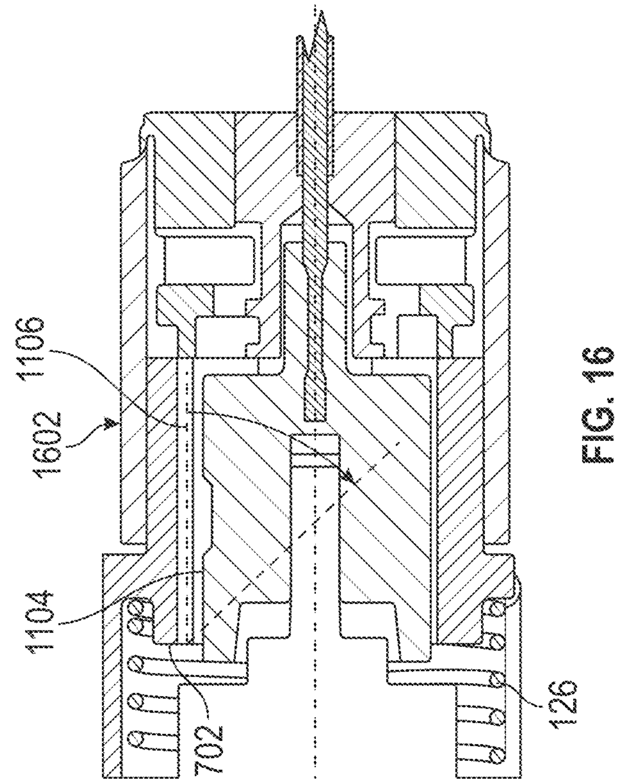
FIG. 16 is a partial sectional view of a barrel, a rotating stylet assembly, and a shield container showing a route of a shield from an open state to a closed state.

FIG. 16 illustrates the shield 128 transitioning from the open state 1502 to the closed state 1602. In the transition, the shield arm 1106 remains attached to the shield base 1104 while also pivoting downward. During the transition the shield base 1104 remains attached to the shield container 202. The stylet 124, being disposed between the closed end 106 of the barrel 102 and the shield 128, prevents accidental exposure of the stylet 124 outside of the open end 104 of the barrel 102.

Figure 17:
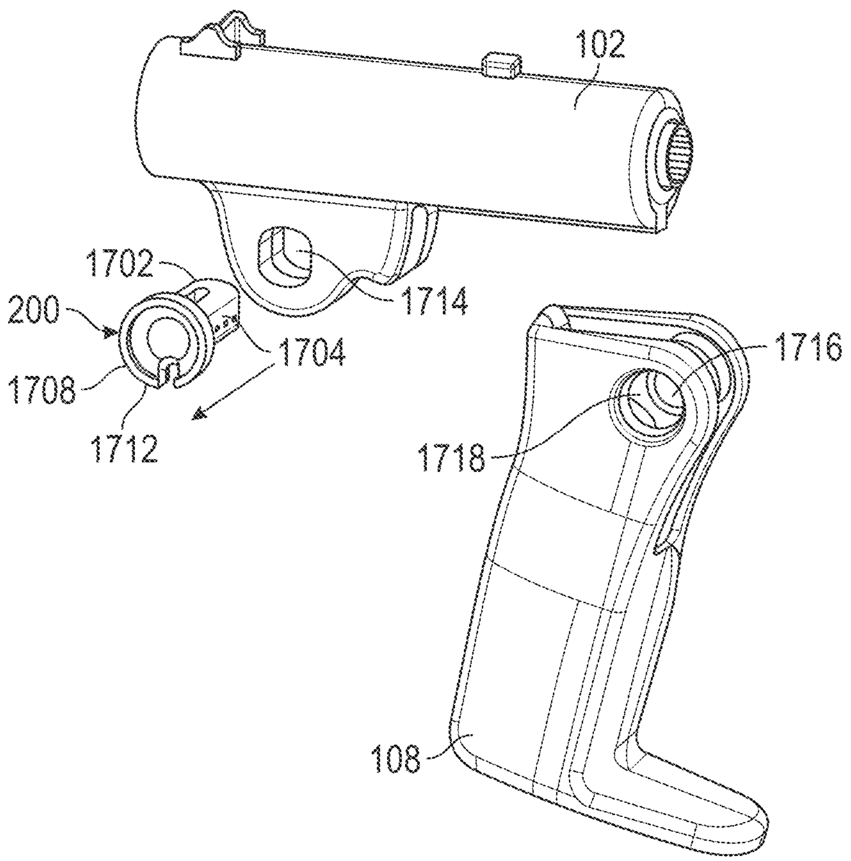
FIG. 17 is an exploded view of an example intraosseous access device including a barrel, a handle, and a pivot body.

FIG. 17 illustrates the intraosseous access device 100 with the pivot body 200 removed and the barrel 102 separated from the handle 108. This feature may allow for easy separation of battery waste and biohazard waste. The pivot body 200 is an independent component from the spring 126, the shield 128, slide interface 120, the release collar 3202, the clutch 3204, and the latch 3206. Each of the seven components is optional, but the intraosseous access device 100 must have at least one. The separable connection between the barrel 102 and the handle 108 enables a handle of an intraosseous access device according to an embodiment, such as handle 108 of intraosseous access device 100, to be used with multiple barrels, such as barrel 102 and another barrel (not illustrated), which could be identical to the initial barrel 102 or different from the initial barrel 102. For example, intraosseous access device access device 100 can be provided with original barrel 102, which can be adapted for establishing intraosseous access, and another barrel adapted for another function, such as delivering medication to the intramedullary space accessed through use of the intraosseous access device 100 with barrel 102 or for obtaining a biopsy sample from the intramedullary space accessed through use of the intraosseous access device 100 with barrel 102. These secondary barrels can include longer housings and/or needles than those of the original barrel 102, for example, as structural adaptations specific for the purpose of the secondary barrels. Indeed, intraosseous access devices according to embodiments can include a single handle and multiple barrels, each of which are identical or different in this or different manners. In these embodiments, the intraosseous access device can include one barrel, such as barrel 102, attached to the handle, such has handle 108, and one or more barrels detached from the handle. This arrangement can be considered advantageous at least because it eliminates the need to attach a barrel to the handle before use of the intraosseous access device. Alternatively, intraosseous access devices according to these embodiments can include a handle and multiple barrels, with none of the barrels initially attached to the handle. This arrangement can be considered advantageous at least because it eliminates the need to detach a barrel from the handle in the event a secondary barrel is desired for initial use of the intraosseous access device.

The pivot body 200 has a first pivot body portion 1702 and a second pivot body portion 1708. The first pivot body portion 1702 may define a first circumference, while the second pivot body portion 1708 may define a second circumference. In some embodiments, the second circumference may be larger than the first circumference. This may allow the insertion of the pivot body 200 into the drill 200 up to a predetermined depth. In particular, the barrel aperture 1714 may be configured to receive the first circumference, but not receive the second circumference. The first pivot body portion 1702 has a first pivot body exterior surface 1704. The second pivot body portion 1708 has a second pivot body interior surface 1712. The barrel 102 has a barrel aperture 1714. The handle 108 has a first handle aperture 1716 and a second handle aperture 1718. When the pivot body 200 is attached to the barrel 102 and handle 108, the barrel aperture 1714 is disposed between the first handle aperture 1716 and second handle aperture 1718, and the pivot body 200 is configured to be disposed within the barrel aperture 1714, the first handle aperture 1716, and the second handle aperture 1718. Also, when the pivot body 200 is attached to the barrel 102 and the handle 108, the intraosseous access device 100 is able to transition between the first pivot position 302 and the second pivot position 402 as the first pivot body exterior surface 1704 is adjacent to the edges of the barrel aperture 1714, the first handle aperture 1716, and the second handle aperture 1718.

Figure 18:
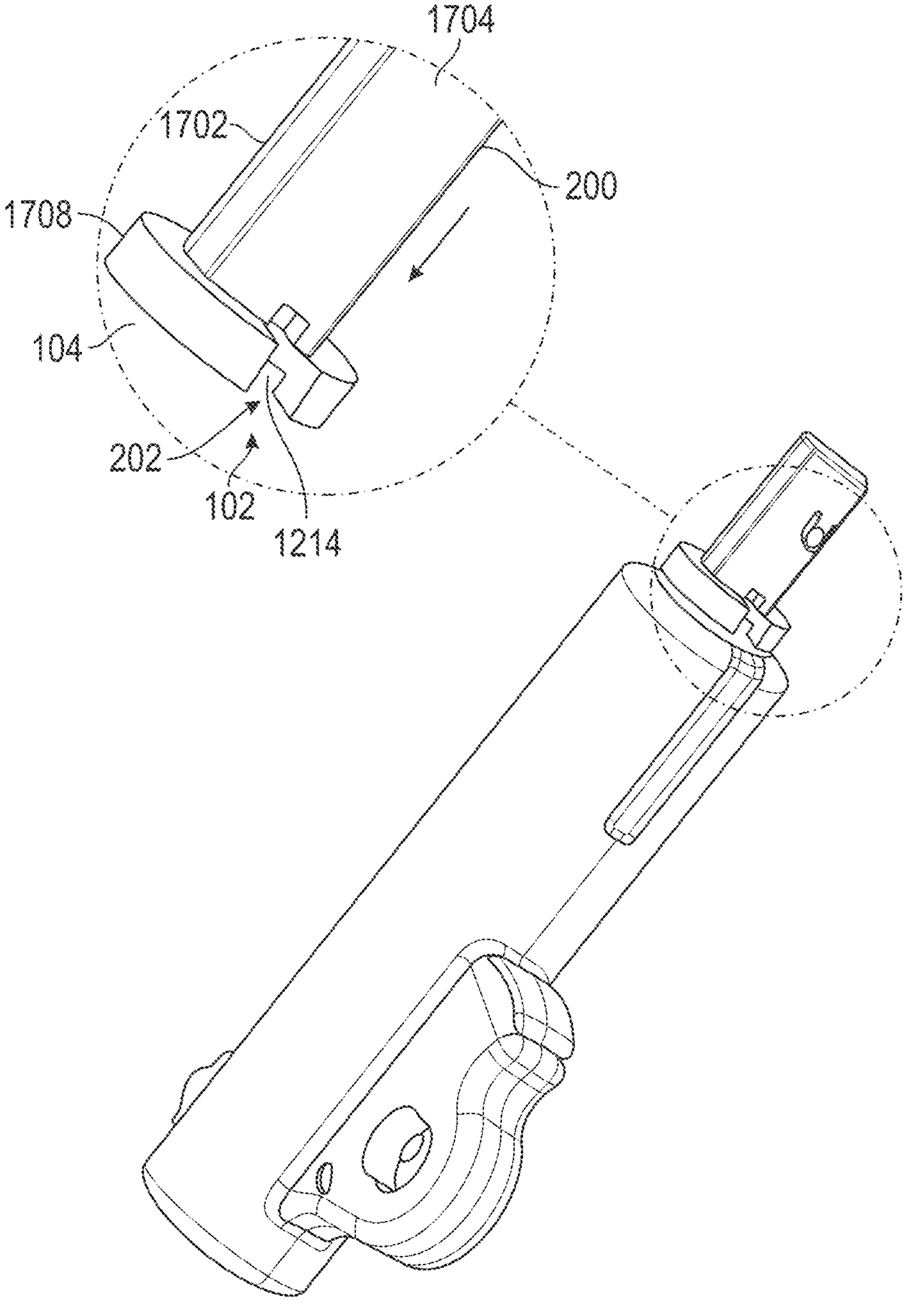
FIG. 18 illustrates an outer surface of a shield container integrated with an inner surface of a pivot body.

FIGS. 18 through 22 illustrate how both ends of the pivot body 200 are used to integrate with the shield container 202 to close the open end 104 of the barrel 102. This form of safety is passive safety as the pivot body 200 closes an open end. This is opposed to the form of active safety which is seen when using the shield 128. FIG. 18 illustrates the barrel 102 with an expanded view of the integration between the shield container 202 and the pivot body 200.

FIG. 18 illustrates the first container portion outer surface 1214 of the shield container 202 integrated with the second pivot body interior surface 1712. This closure of the shield container 202, prevents the stylet 124 from actuating through the first pivot body portion 1702 of the pivot body 200. As shown, the pivot body 200 may be configured to snap on the open end of the barrel 102. This snapping mechanism allows handling of a spent barrel 102 without exposing a user to hazards that may be presented by a used stylet 124. While a snapping mechanism is shown, other embodiments may include a fitted mechanism that may use traction between the barrel 102 and the pivot body 200, a screw mechanism between the barrel 102 and the pivot body 200, etc. Further, while the pivot body 200 is shown to be generally disposed externally to the barrel 102, some embodiments may feature a pivot body 200 that is sized to fit generally within the open end of the barrel 102.

Figure 19:
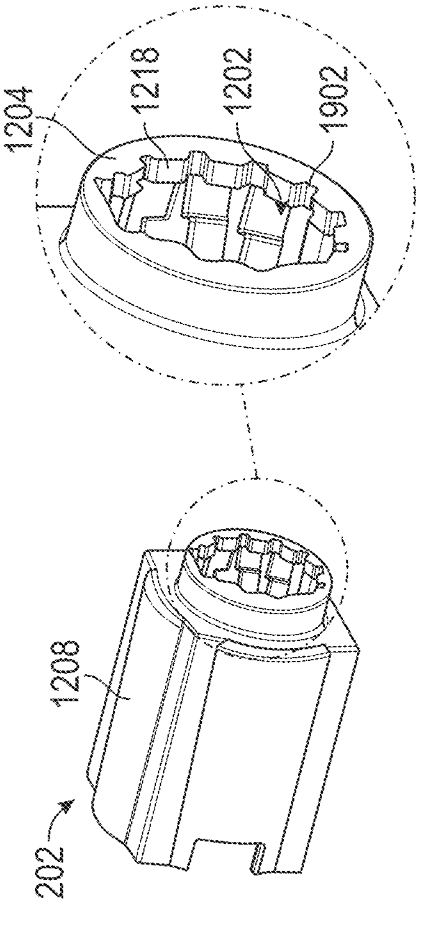
FIG. 19 illustrates a shield container with an expanded view showing concave grooves on an inner surface.

FIG. 19 illustrates an embodiment of the shield container 202 with an expanded view of the first container portion 1204. The container inner surface 1218 of the embodiment has concave grooves 1902. These concave grooves 1902 may be used as various fixtures to the drill 100. As shown, the grooves are concave, however, in other embodiments, the grooves may be convex. Further, while concave grooves may be configured to interact with ridges, other embodiments of the inner surface 1218 may define ridges.

Figure 20:
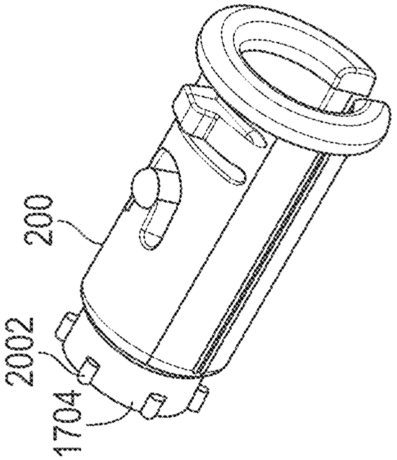
FIG. 20 illustrates a pivot body with convex ridges along an outer surface.

FIG. 20 illustrates an embodiment of the pivot body 200. The first pivot body exterior surface 1704 of the embodiment has convex ridges 2002. The convex ridges 2002 may be disposed about a perimeter of the pivot body 200. The convex ridges 2002 may be protruding generally perpendicular to the pivot body 200. The convex ridges 2002 may be protruding outward from the pivot body 200. The concave grooves 1902 on the container inner surface 1218 of the shield container 202 and the convex ridges 2002 on the first pivot body exterior surface 1704 of the pivot body 200 are mating surfaces. While exterior surface 1704 includes convex ridges, other embodiments may define convex grooves.

Figure 21:
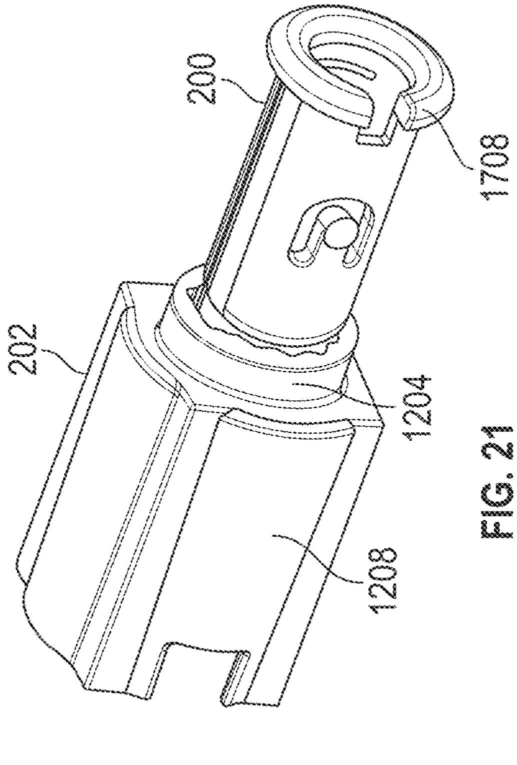
FIG. 21 illustrates an inner surface of a shield container integrated with an outer surface of a pivot body.

FIG. 21 shows the shield container 202 and the pivot body 200 integrated. The concave grooves 1902 on the container inner surface 1218 of the shield container 202 are adjacent to the convex ridges 2002 on the first pivot body exterior surface 1704 of the pivot body 200. The integration of the shield container 202 and the pivot body 200 prevents the stylet 124 from actuating through the first pivot body portion 1702 of the pivot body 200.

Figure 22:
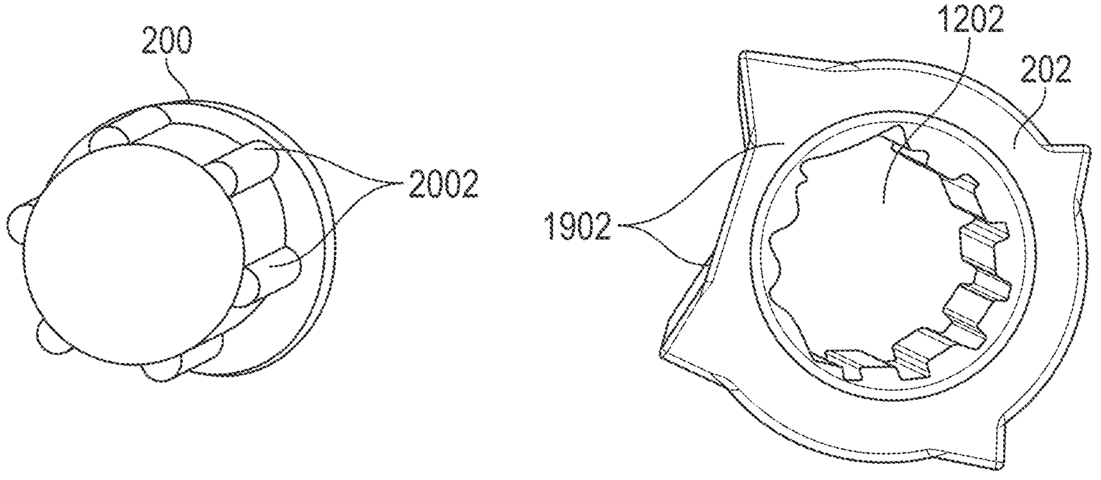
FIG. 22 illustrates a shield container with concave grooves on an inner surface and a pivot body with convex ridges along an outer surface.

FIG. 22 illustrates one embodiment of the shield container 202 and one embodiment of the pivot body 200. The shield 128 is in an open state 1502. The container inner surface 1218 of the embodiment has concave grooves 1902. The first pivot body exterior surface 1704 of the embodiment has convex ridges 2002. The concave grooves 1902 on the container inner surface 1218 of the shield container 202 and the convex ridges 2002 on the first pivot body exterior surface 1704 of the pivot body 200 are mating surfaces.

Figure 23:
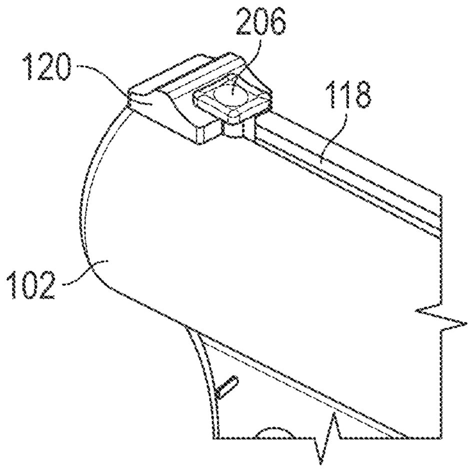
FIG. 23 illustrates a slide interface and a button assembly in a retracted position inside of a slide channel.
Figure 24:
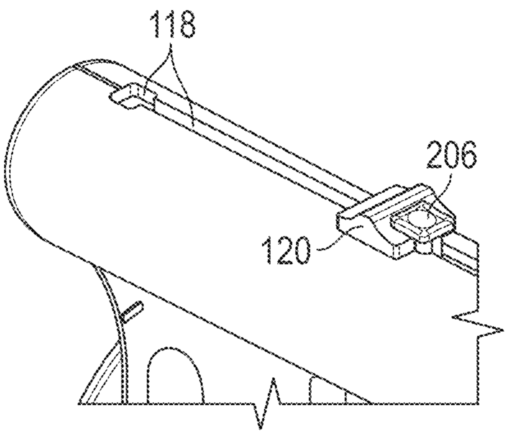
FIG. 24 illustrates a slide interface and a button assembly in an actuated position inside of a slide channel.
Figure 25:
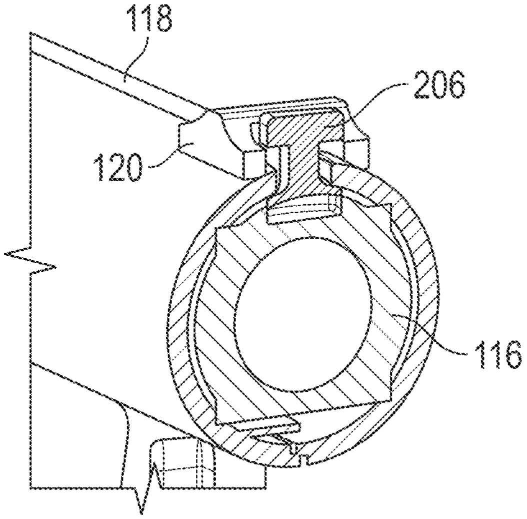
FIG. 25 illustrates slide interface, a button assembly, slide carrier, and barrel showing the slide interface and button assembly in an actuated position.
Figure 27:
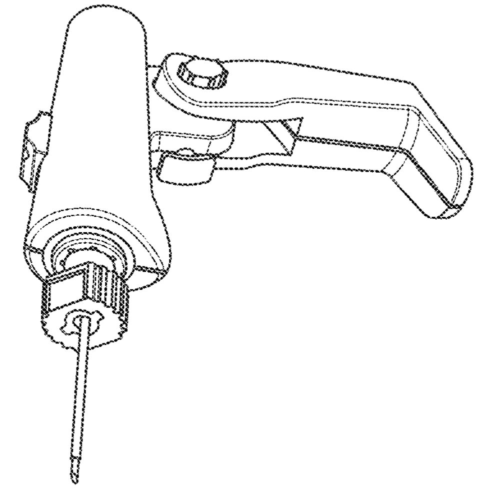
FIG. 27 illustrates another example intraosseous access device.
Figure 29:
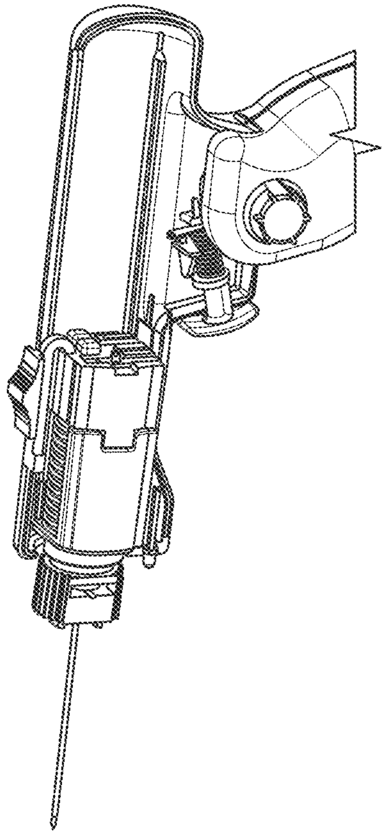
FIG. 29 illustrates another view of the example intraosseous access device illustrated in FIG. 28.
Figure 26:
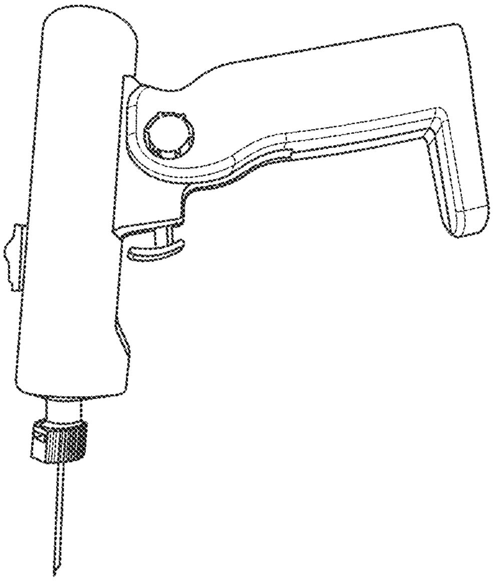
FIG. 26 illustrates another example intraosseous access device.
Figure 28:
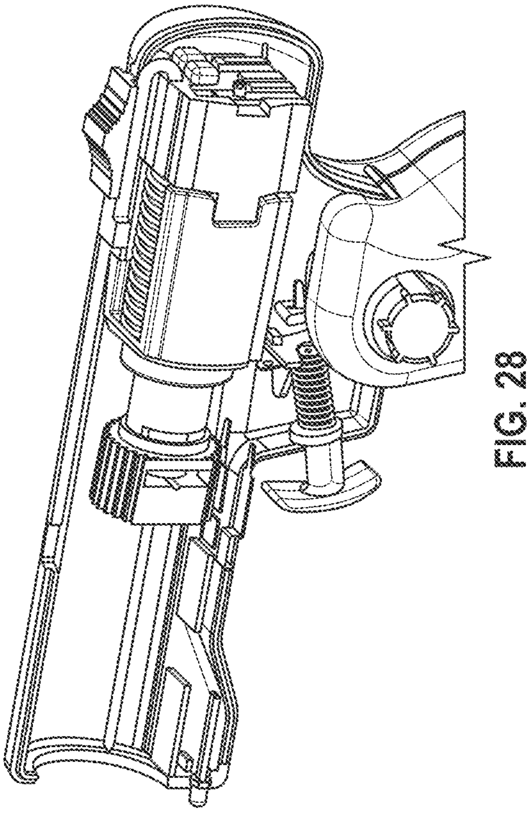
FIG. 28 illustrates another example intraosseous access device having a release mechanism with a secondary button located near the front of the barrel, which may be either on top or on the side. Internally, it may actuate a latch pawl that locks the spindle, allowing the user to twist the barrel 90 degrees to detach the cannula. The button may simultaneously unlatch the motor slide mechanism, so that when the user releases the button the stylet will automatically retract.
Figure 30:
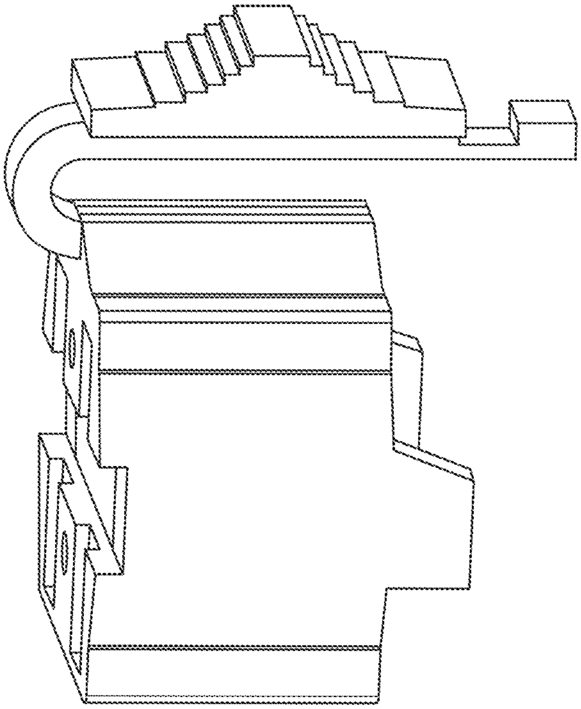
FIG. 30 illustrates an isolated view of the secondary button of the example intraosseous access device illustrated in FIG. 28.
Figure 31A:
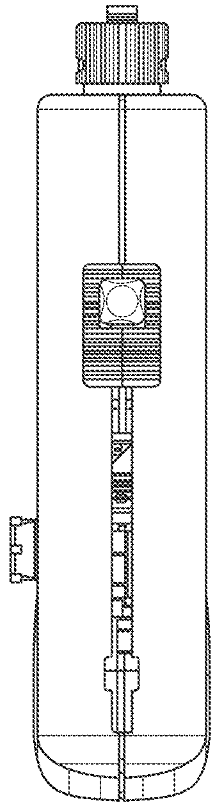
FIG. 31A illustrates a view of another example intraosseous access device having indicia on one or more components of the device to aid in use of the device.
Figure 31B:
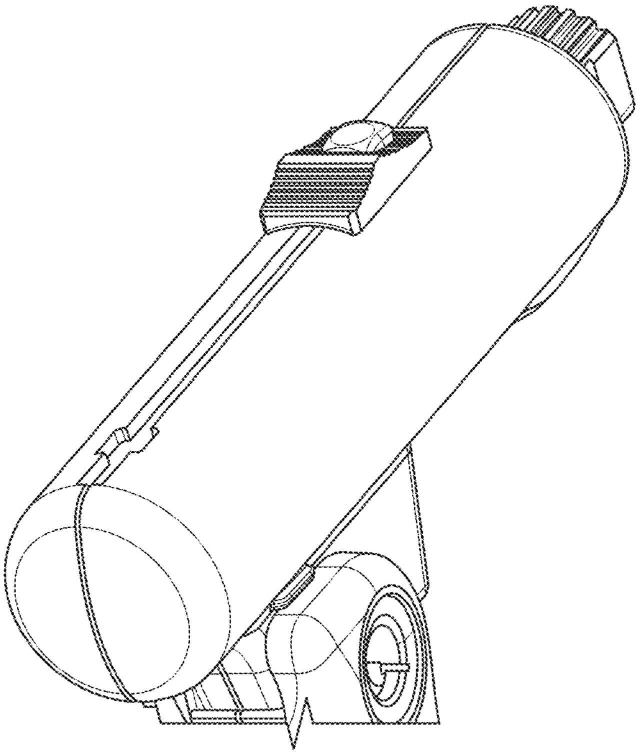
FIG. 31B illustrates another view of the example intraosseous access device having indicia on one or more components of the device to aid in use of the device.

FIGS. 23 through 25 illustrate the slide interface 120 and button assembly 206 inside the slide channel 118 and adjacent to top of the barrel 102. The slide interface 120 is an independent component from the spring 126, the shield 128, the pivot body 200, the release collar 3202, the clutch 3204, and the latch 3206. Each of the seven components is optional, but the intraosseous access device 100 must have at least one.

FIG. 23 illustrates the slide interface 120 and button assembly 206 in a retracted position. The portion of the slide interface 120 within the slide channel 118 is fully retracted in the slide channel 118 towards the closed end 106 of the barrel 102.

FIG. 24 illustrates the slide interface 120 and button assembly 206 in an actuated position. The portion of the slide interface 120 within the slide channel 118 is fully actuated in the slide channel 118 towards the open end 104 of the barrel 102.

FIG. 25 illustrates a cross-sectional view of the slide carrier 116, button assembly 206, slide interface 120, and barrel 102. The slide carrier 116 is configured with space for the button assembly 206 to compress. The compression of the button assembly may allow for movement of the slide carrier 116. The decompression of the button assembly 206 may allow for stability of the slide carrier 116.

Figure 32A:
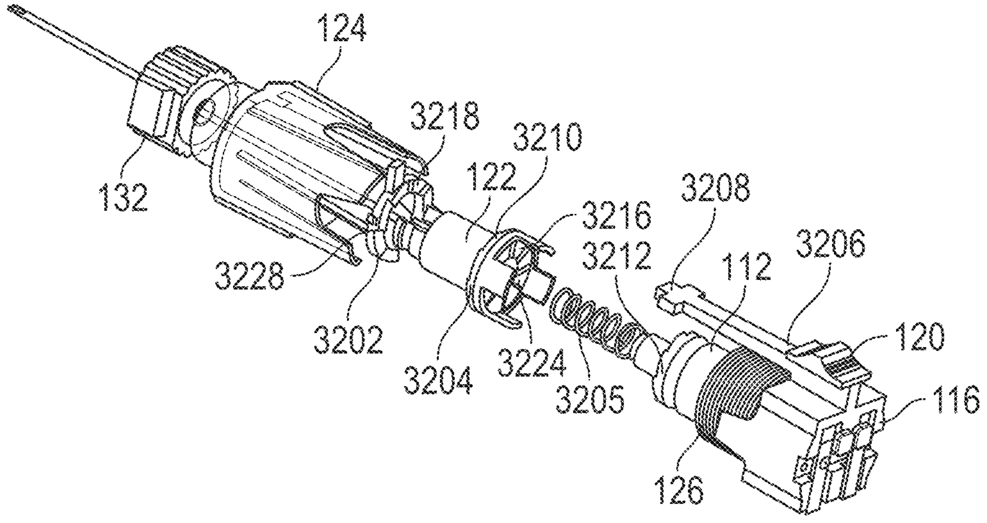
FIG. 32A illustrates an exploded view of a motor, a slide carrier, a slide interface, a spring, a cannula assembly, a release collar, a clutch, a latch, and a latch tab.
Figure 32B:
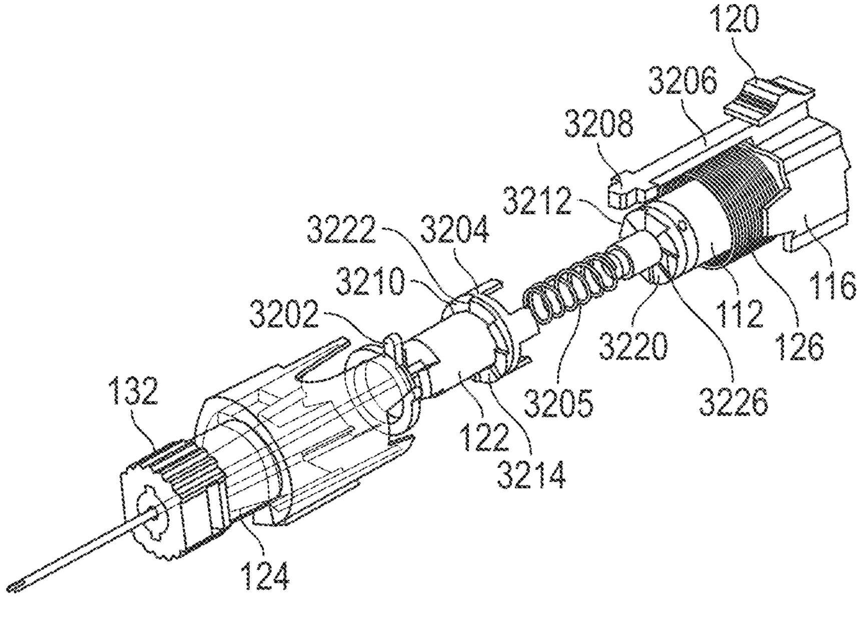
FIG. 32B illustrates another exploded view of the motor, the slide carrier, the slide interface, the spring, the cannula assembly, the release collar, the clutch, the latch, and the latch tab.

FIG. 32 illustrates two exploded views of an embodiment of the intraosseous access device 100. The motor 112 is shown partially disposed inside the spring 126. The spring 126 is in a compressed state and disposed adjacent to the slide carrier 116. Attached to the slide carrier 116 and slide interface 120 is a latch 3206. At an end of the latch 3206 is a latch tab 3208 shaped to fit inside a slide channel window 3302. The slide channel window 3302 is a portion of the slide channel 118 with a wider opening. The latch 3206 may fit inside the slide channel 118. The latch tab 3208 may not fit inside portions of the slide channel 118. The slide carrier 116 can actuate throughout the barrel 102 while the latch 3206 is inside the slide channel 118 and while the latch tab 3208 is inside of the barrel 102. The slide carrier 116 can actuate throughout the barrel 102 while the latch 3206 is inside the slide channel 118 and while the latch tab 3208 is and outside of the barrel 102.

A clutch 3204 is disposed between the motor 112 and the rotating stylet assembly 122. The clutch 3204 may be composed of a first clutch plate 3210, a second clutch plate 3212, and a clutch spring 3205. The first clutch plate 3210 is attached to the rotating stylet assembly 122. The second clutch plate 3212 is attached to the motor 112. The clutch spring 3205 is disposed between the first clutch plate 3210 and the second clutch plate 3212. The first clutch plate 3210 has a first clutch plate front side 3214 and a first clutch plate back side 3216. The second clutch plate 3212 has a second clutch plate front side 3220. The first clutch plate front side 3214 has first clutch plate convex wedges 3222 and the first clutch plate back side 3216 has first clutch plate concave wedges 3224. The second clutch plate front side 3220 has second clutch plate convex wedges 3226. Without force applied to the stylet 124, the clutch 3204 is in a disengaged position because of the presence of the clutch spring 3205. When the clutch 3204 is disengaged, the clutch plate front side 3214 is disposed adjacent to a release collar 3202. The release collar 3202 has a release collar back side 3218. The release collar back side 3218 has release collar concave wedges 3228. When the clutch is disengaged, the first clutch plate convex wedges 3222 are disposed adjacent to the release collar concave wedges 3228. When the clutch 3204 is disengaged, actuation of the motor 112 will not rotate the rotating stylet assembly 122. The concave and convex wedges may be in any shape that cause mating surfaces. When the clutch 3204 is disengaged, contact of the first clutch plate convex wedges 3222 to the release collar concave wedges 3228 may prevent rotation of the cannula assembly 132, rotating stylet assembly 122, release collar 3202, and first clutch plate 3210 when the intraosseous access device 100 is rotated and the cannula assembly 132 is held unrotated.

The stylet 124 may pierce skin and contact bone, allowing the operator of the intraosseous access device 100 to apply drilling force. This drilling force may compress the clutch spring 3205 and dispose the first clutch plate concave wedges 3224 adjacent to the second clutch plate convex wedges 3226, therefore engaging the clutch 3204. When the clutch 3204 is engaged, actuation of the motor 112 will rotate the rotating stylet assembly 122.

In this embodiment, a cannula assembly 132 is attached to the rotating stylet assembly 122. Rotation of the intraosseous access device 100, while the cannula assembly 132 remains unrotated, will also prevent rotation of the rotating stylet assembly 122, and release collar 3202. The cannula assembly 132 may detach from the rotating stylet assembly 122.

Figure 33:
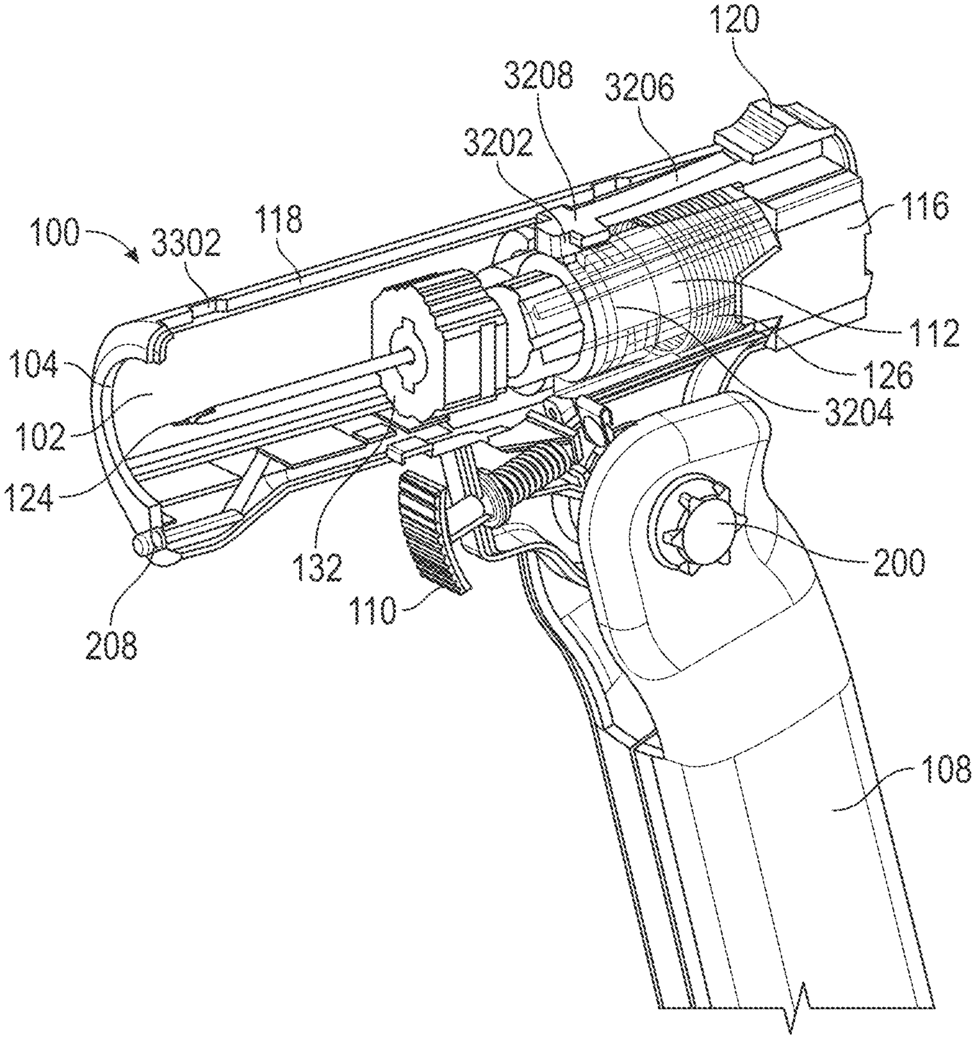
FIG. 33 illustrates an intraosseous access device in a retracted position and the latch tab inside the barrel.

FIG. 33 illustrates an embodiment of the intraosseous access device 100 in a retracted position. The rotating stylet assembly 122 is encircled by the release collar 3202. The clutch 3204 is disengaged and adjacent to the release collar 3202. The slide interface 120 may be actuated relatively parallel to the barrel 102, moving other components toward the open end 104 of the barrel 102, until the intraosseous access device 100 is in an activated position. The latch 3206 is partially inside the slide channel 118 and partially inside the barrel 102. The latch 3206 is configured to actuate throughout the slide channel 118 and barrel 102 until the intraosseous access device 100 is in an activated position. The latch tab 3208, inside the barrel 102, is configured to actuate throughout the barrel 102 until the intraosseous access device 100 is in an activated position.

Figure 34A:
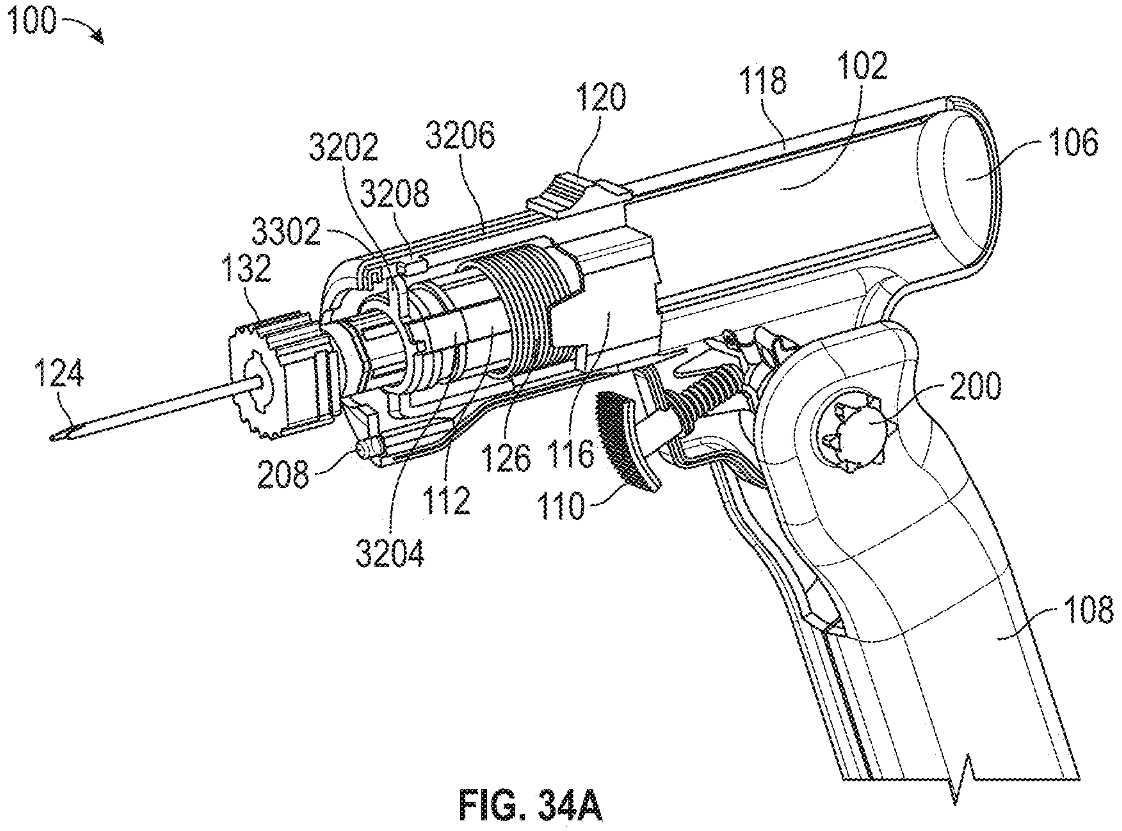
FIG. 34A illustrates a view of an intraosseous access device in an actuated position, the clutch in a deactivated position, and the latch tab inside a slide channel window.
Figure 34B:
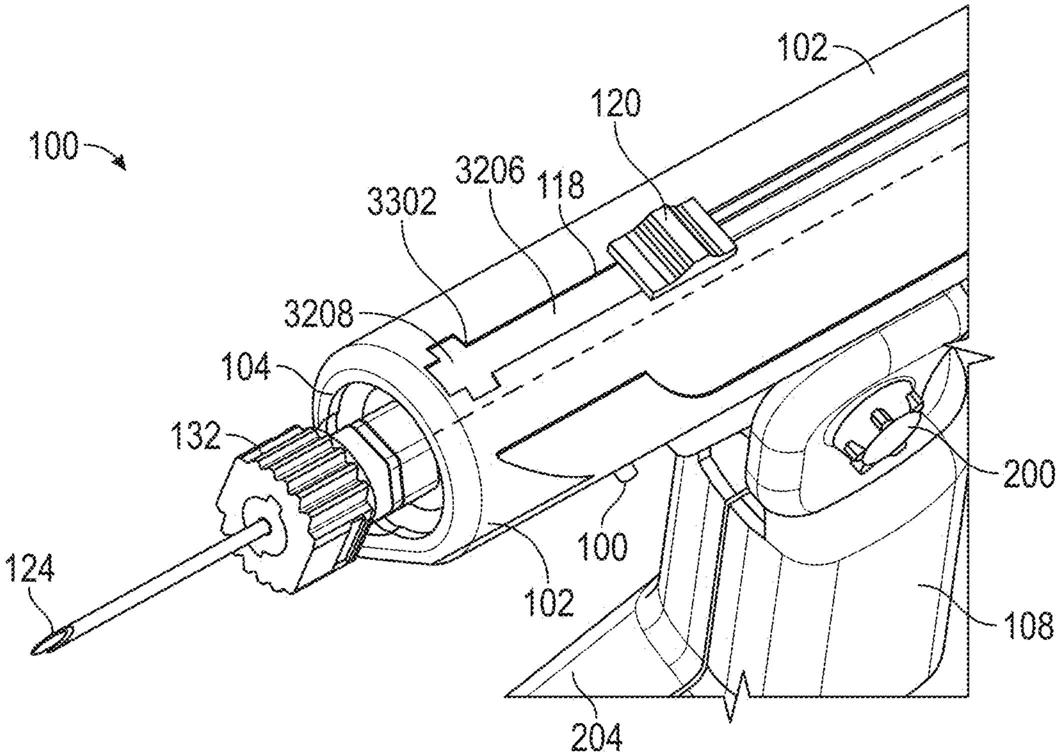
FIG. 34B illustrates another view of the intraosseous access device in the actuated position, the clutch in the deactivated position, and the latch tab inside a slide channel window.

FIG. 34 illustrates two views of an embodiment of an intraosseous access device 100 in an activated position. The clutch 3204 is in a disengaged position and adjacent to the release collar 3202. The rotating stylet assembly 122 is encircled by the release collar 3202. The latch 3206 is inside the slide channel 118 and the latch tab 3208 is inside the slide channel window 3302. The spring 126 is in a compressed state when the device is sliding from a deactivated position to an activated position. The spring 126 may compress more when the intraosseous device 100 enters an activated position. The clutch 3204 is disengaged as there is no drilling force applied to the stylet 124.

Figure 35:
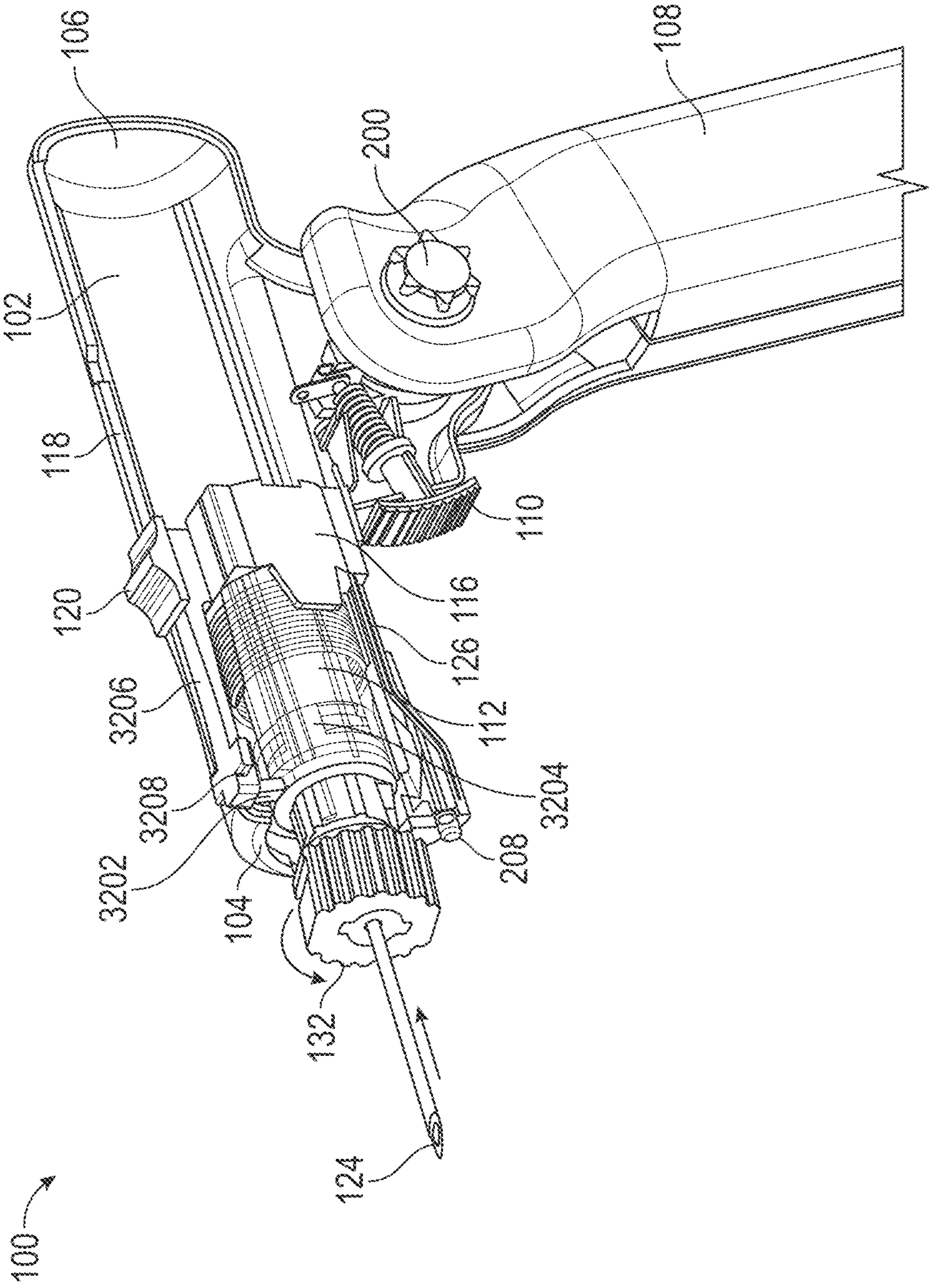
FIG. 35 illustrates an intraosseous access device in an actuated position, the clutch in an engaged position, and the latch tab inside the slide channel window.

FIG. 35 illustrates an embodiment of the intraosseous access device 100. The intraosseous access device 100 is in an actuated position and the rotating stylet assembly 122 is encircled by the release collar 3202. The clutch 3204 is in an engaged position as there is drilling force applied to the stylet 124. Rotation of the rotating stylet assembly 122 including the stylet 124 may be caused by actuation of the motor 112. The latch 3206 is inside the slide channel 118, and the latch tab 3208 is inside the slide channel window 3302. The spring 126 within the device is in a compressed state.

Figure 36:
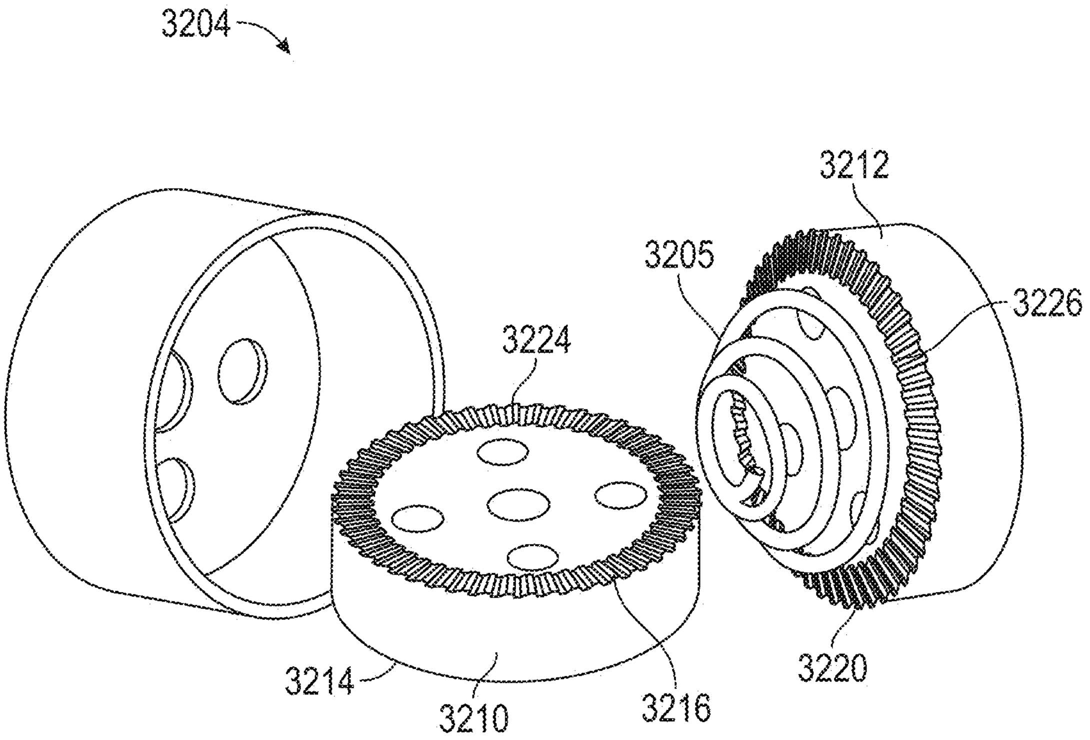
FIG. 36 illustrates a disassembled clutch of an example intraosseous access device.

FIG. 36 illustrates an embodiment of the clutch 3204 in a disassembled state. In this embodiment the first clutch plate concave wedges 3224 and the second clutch plate convex wedges 3226 are in a shorter ridged style. Without drilling force, the clutch spring 3205 will prevent the clutch 3204 from entering an engaged position. The clutch spring 3205 may be compressed by drilling force applied to the stylet 124. The clutch 3204 may enter an engaged position with compression of the clutch spring 3205.

Figure 37:
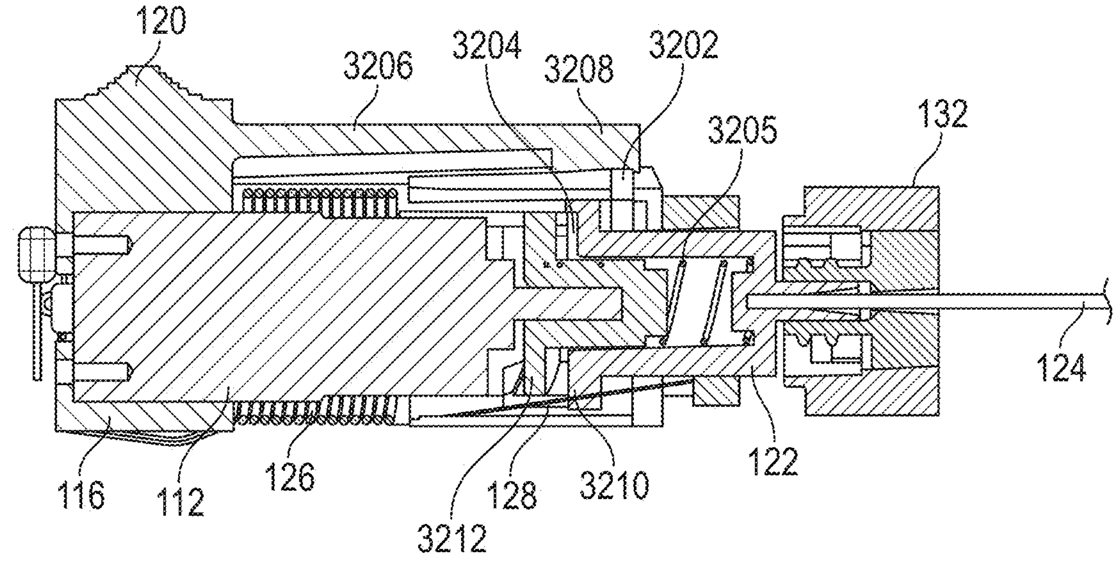
FIG. 37 illustrates a partial sectional view of a slide carrier, a slide interface, a latch, a latch tab, a spring, a motor, a clutch, a release collar, and a cannula assembly of an example intraosseous access device with the clutch in a disengaged position.

FIG. 37 illustrates a partial sectional view of a slide carrier 116, a slide interface 120, a latch 3206, a spring 126, a motor 112, a rotating stylet assembly 122, a clutch 3204, a release collar 3202, and a cannula assembly 132. The cannula assembly 132 is attached to the rotating stylet assembly 122. The clutch 3204 is in a disengaged position as there is no drilling force applied to the stylet 124. The lack of drilling force is leaving the clutch spring 3205 in a decompressed state. The first clutch plate front side 3214 is contacting the release collar back side 3218. Actuation of the motor 112 will not rotate the rotating stylet assembly 122.

Figure 38:
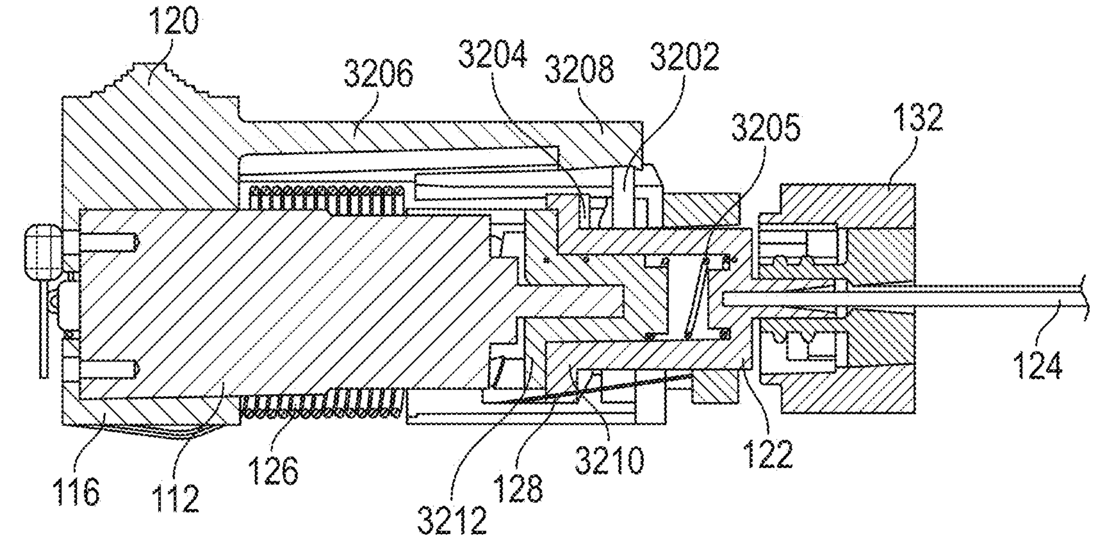
FIG. 38 illustrates a partial sectional view of a slide carrier, a slide interface, a latch, a latch tab, a spring, a motor, a clutch, a release collar, and a cannula assembly of an example intraosseous access device with the clutch in an engaged position.

FIG. 38 illustrates a partial sectional view of a slide carrier 116, a slide interface 120, a latch 3206, a spring 126, a motor 112, a rotating stylet assembly 122, a clutch 3204, a release collar 3202, and a cannula assembly 132. The cannula assembly 132 is attached to the rotating stylet assembly 122. The clutch 3204 is in an engaged position and the clutch spring is compressed as there is drilling force applied to the stylet 124. Actuation of the motor 112 will rotate the rotating stylet assembly 122.

Figure 39A:
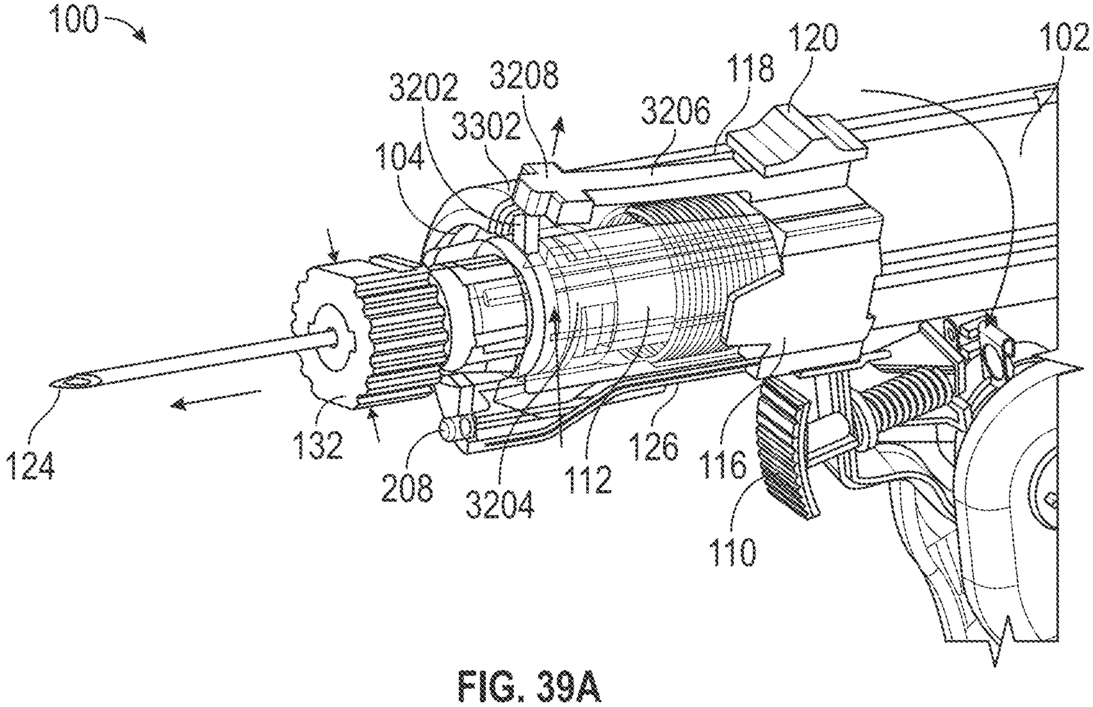
FIG. 39A illustrates a view of an intraosseous access device in a rotated state with the cannula assembly, rotating stylet assembly, and release collar of an example intraosseous access device with the release collar in an unrotated state causing part of the release collar to protrude into the slide channel window, further causing the removal of the latch tab from the slide channel window.
Figure 39B:
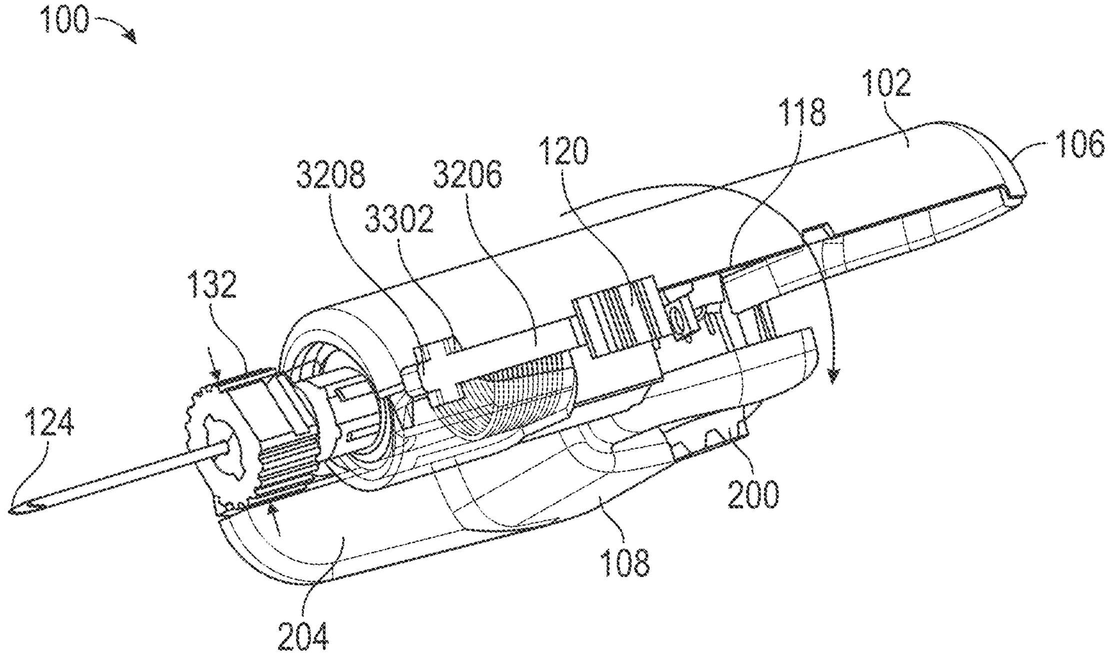
FIG. 39B illustrates another view of the intraosseous access device in the rotated state with the cannula assembly, rotating stylet assembly, and release collar of the example intraosseous access device with the release collar in the unrotated state causing part of the release collar to protrude into the slide channel window, further causing the removal of the latch tab from the slide channel window.

FIG. 39 illustrates two views of an embodiment of the intraosseous access device 100 in a rotated state with a cannula assembly 132 in an unrotated state. A user of the device can complete rotation of the intraosseous access device 100 with one hand while holding the cannula assembly 132 unrotated with the other hand. Rotation of the intraosseous access device 100, while the cannula assembly 132 remains unrotated, will also prevent rotation of the rotating stylet assembly 122 and the release collar 3202. This counteracting movement will cause part of the release collar 3202 to protrude into the slide channel window 3302 removing the latch tab 3208 from the slide channel window 3302. Similar counteracting movement may also disconnect the cannula hub from the intraosseous access device 100.

Figure 40:
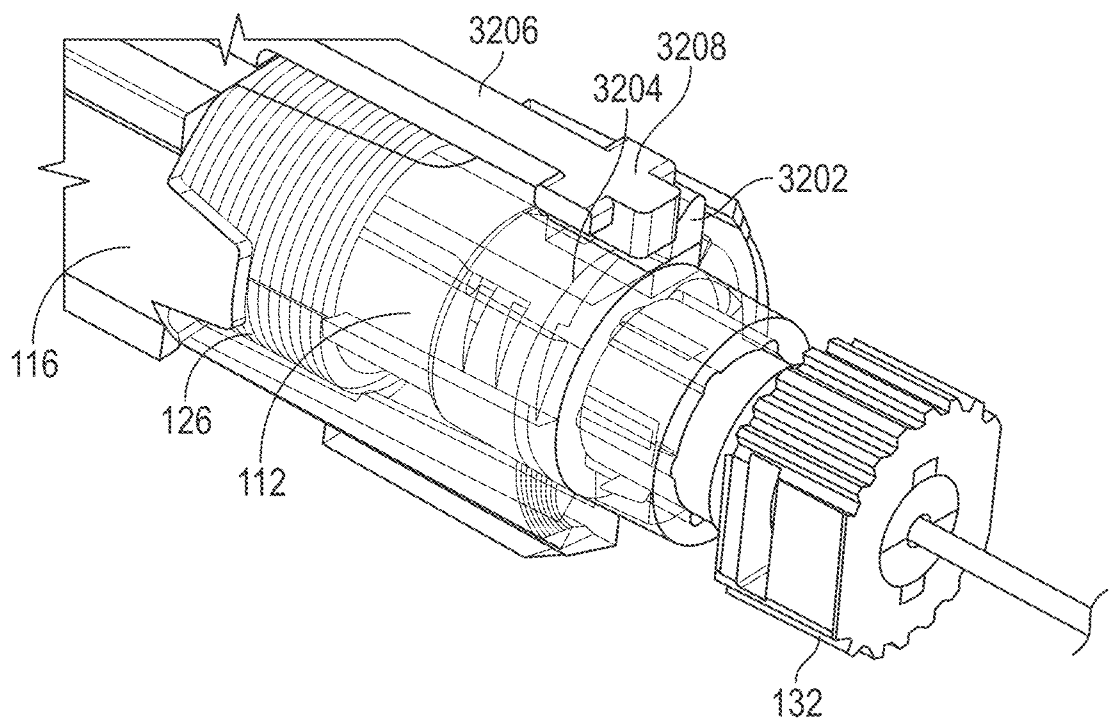
FIG. 40 illustrates the slide carrier, latch, and latch tab of an example intraosseous access device with the latch tab in an unrotated state with the cannula assembly, rotating stylet assembly, and release collar in an unrotated state, the release collar adjacent to the latch tab.

FIG. 40 illustrates the spring 126, slide carrier 116, latch 3206, latch tab 3208, cannula assembly 132, release collar 3202, and rotating stylet assembly 122 in an unrotated state. The clutch 3204 is in a disengaged position and the first clutch plate 3210 is contacting the release collar 3202. During rotation of the intraosseous access device 100, the release collar 3202 remains unrotated when the cannula assembly 132 is being held unrotated. In this state the latch 3206 is unbent and the release collar 3202 is not causing movement of the latch tab 3208.

Figure 41:
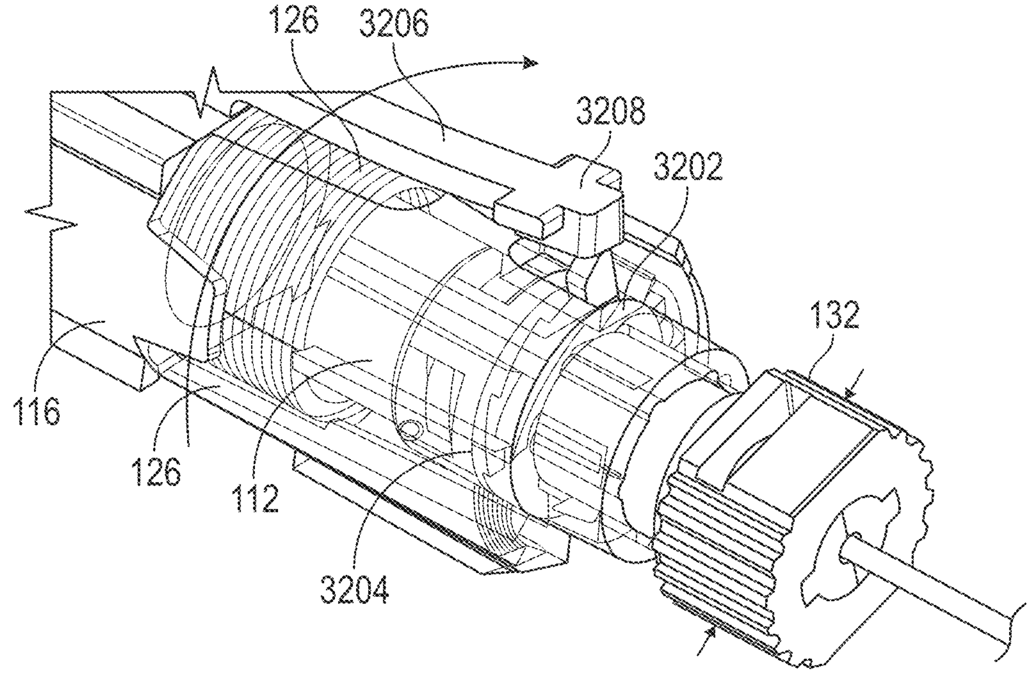
FIG. 41 illustrates the slide carrier, latch, and latch tab in a rotated state with the cannula assembly, rotating stylet assembly, and release collar in an unrotated state causing contact between the release collar and latch tab, bending of the latch, and outward movement of the latch tab.

FIG. 41 illustrates the slide carrier 116, latch 3206, and latch tab 3208 in a rotated state and the cannula assembly 132, release collar 3202, and rotating stylet assembly 122 in an unrotated state causing contact between the release collar 3202 and latch tab 3208 and movement of the latch tab 3208. This contact and further rotation causes further protrusion of the release collar 3204 into the slide channel window 3302, outward movement of the latch tab 3208, and bending of the latch 3206.

Figure 42:
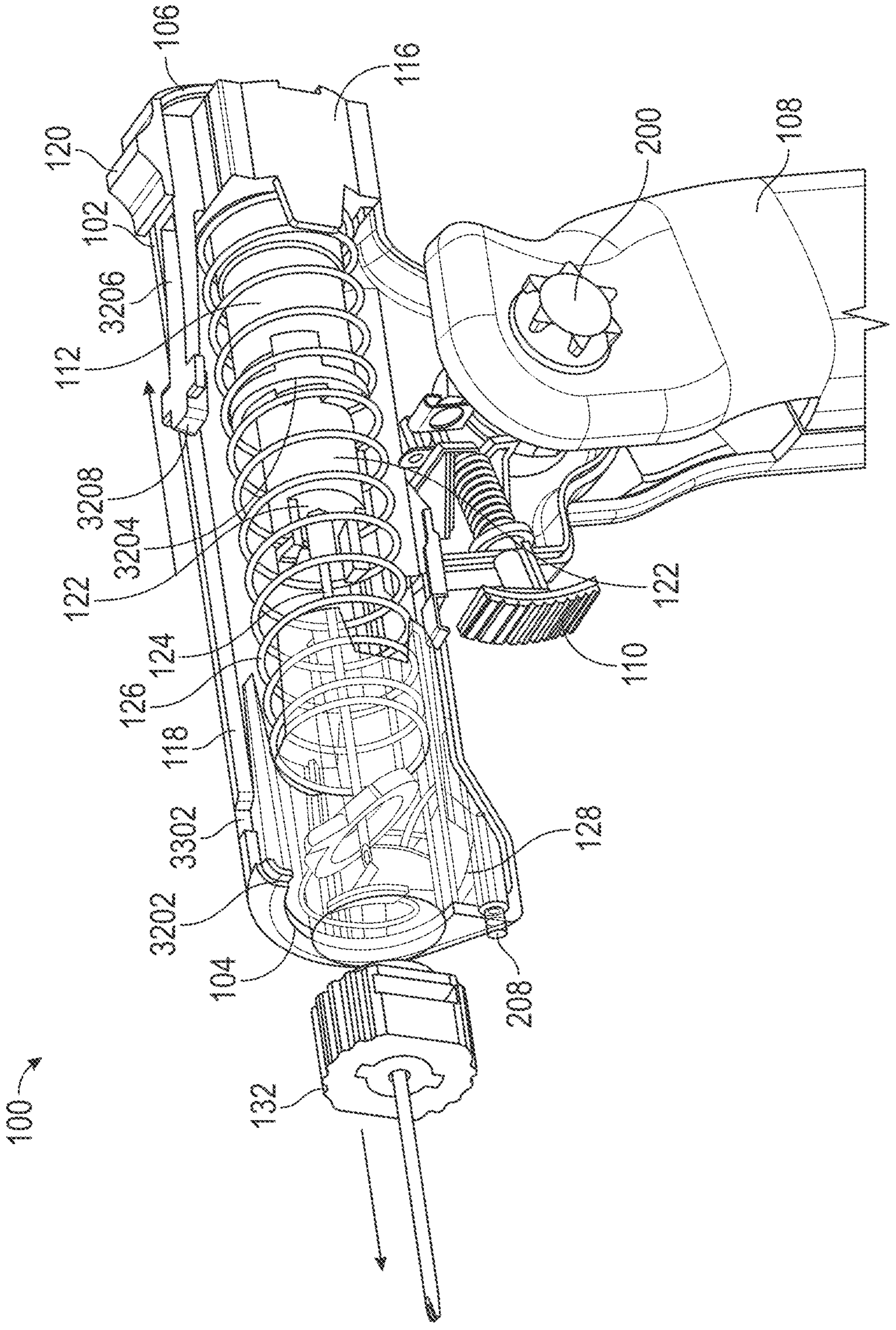
FIG. 42 illustrates an intraosseous access device separated from a cannula assembly with a slide carrier in a retracted position, a spring in a decompressed state, a dislodged release collar inside of the barrel, and a latch tab outside of the barrel.

FIG. 42 illustrates an intraosseous access device 100 separated from a cannula assembly 132. Rotation of the intraosseous device 100 without rotation of the cannula assembly 132 may cause the latch tab 3208 to be removed from the slide channel window 3302 and the cannula assembly 132 to be disconnected from the rotating stylet assembly 122. The spring 126 may move to a decompressed state moving the slide carrier 116 into a retracted position. The release collar 3202 may become dislodged inside the barrel 102. During and after the retraction of the slide carrier 116, the latch 3206 will actuate inside the slide channel 118 and the latch tab 3208 will actuate along the outside of the barrel 102. The shield 128 engages when the slide carrier 116 moves into a retracted position.

Figure 43:
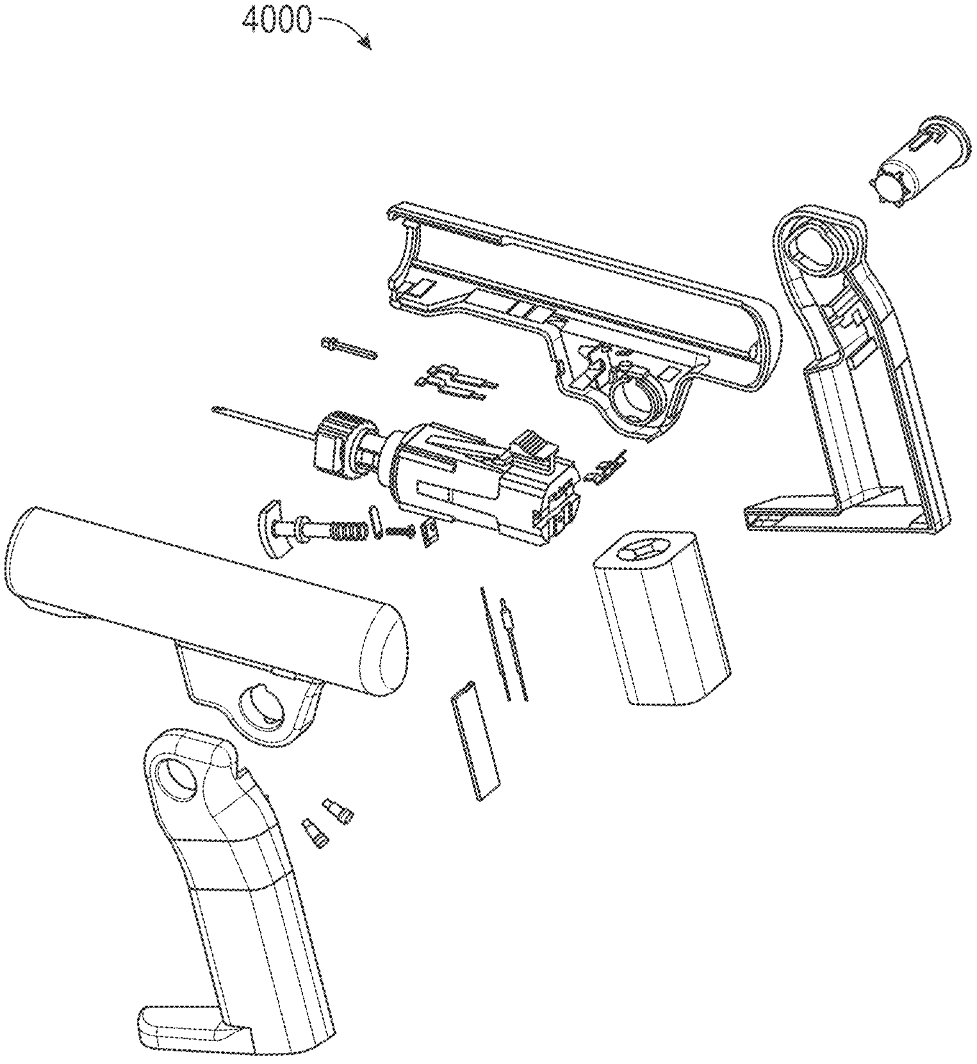
FIG. 43 is an exploded view of another example intraosseous access device.
Figure 44:
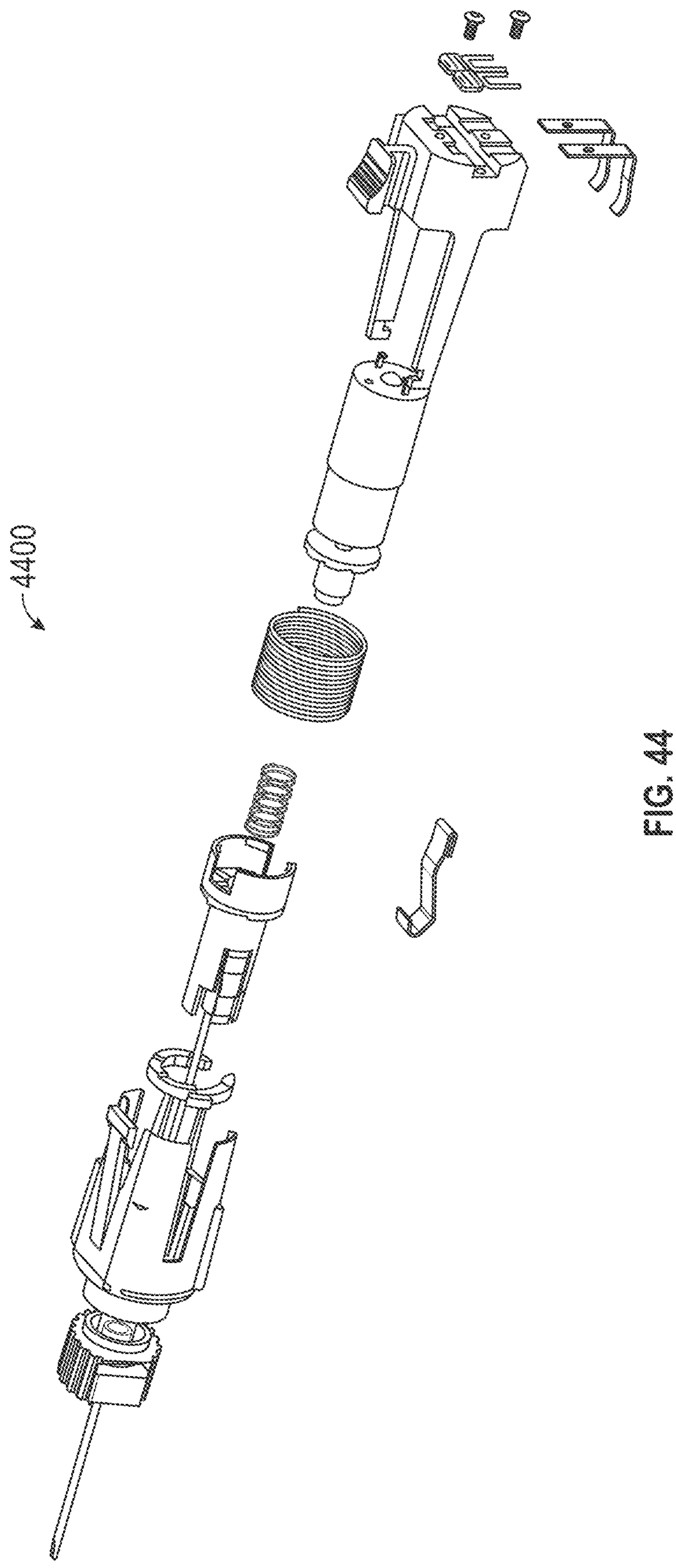
FIG. 44 is an exploding view of the drive assembly of the example intraosseous access device illustrated in FIG. 43.

FIG. 43 illustrates, in exploded form, another example intraosseous access device 4000, which includes the components and assemblies as illustrated and labeled in the Figure. FIG. 44 illustrates, in exploded form, the drive 4400 assembly of the intraosseous access device 4000, which includes a cannula subassembly, motor housing, one-way clutch collar, stylet hub subsassembly, clutch spring, sharp shield, retraction spring, motor hub, motor, motor slide, and electrical contacts as illustrated and labeled in the Figure.

Intraosseous access devices according to embodiments can be used in a variety of procedures, including establishing access to an intramedullary space, delivery of medicine to a location in a body, such as an intramedullary space, and obtaining of biopsy or other tissue samples from a body. Intraosseous access devices according to embodiments can include adaptations for use in specific procedures. For example, an intraosseous access device intended for use in biopsy or other tissue sample obtention procedures can include a specialized needle, such as a needle having a longer length than those described above and illustrated in the figures, and/or a needle having a structure configured for obtaining a biopsy sample from tissue into which the needle is inserted. For example, a needle in a device according to these embodiments can include a notch or other structural feature intended for securing or otherwise containing a tissue sample during removal of the needle from tissue. Intraosseous access devices are also useful in establishing and maintaining intraosseous access for continued delivery of medication to an intraosseous or other space. For example, following a medical procedure involving bone, such as a knee or shoulder replacement or revision, the needle of an intraosseous access device according to an embodiment can be left in situ, with a defined access path to an intramedullary space or other location in the body region affected by the procedure. The needle can be detached from the remainder of the intraosseous access device and left in place to maintain the access path for a period of time, such as hours, days, weeks, months, or longer. A caregiver, or the patient, can then introduce medicine through the needle and into the intramedullary space or other location. Useful medicines in these methods can include antibiotics or other medicines intended to prevent or reduce infection, pain medications, and other medicines. A cover, such as a self-sealing member can be attached to the portion of the needle remaining outside of the body to facilitate repeated introduction of medicines.

Intraosseous access devices according to embodiments are suitable for use in a variety of locations in the body, including long bones, such as the femur, and other locations, including the arm, shoulder, knee, and cranium.

Intraosseous access devices according to embodiments are advantageously provided as a sterilized device. Indeed, intraosseous access devices according to embodiments are advantageously included in sterilized kits that contain all components needed to perform an intraosseous procedure, such as a procedure to establish access to the intraosseous space of a bone. These kits advantageously include a fully assembled intraosseous access device according to an embodiment and an associated sterile needle, for example. This is considered advantageous at least because the kit requires no sterilization or assembly of components before use of the intraosseous access device, enabling efficient use in emergency situations. Also advantageously, intraosseous access devices according to embodiments are provided in a folded configuration, such as the configuration illustrated in FIG. 3. This ensures that the electrical contacts remain in a disconnected state during shipment and storage, avoiding undesired discharge of an electrical power supply, such as a battery, in the drill. Also, in embodiments that include a light, the light is advantageously energized upon moving the intraosseous access device into the unfolded configuration, such as the configuration illustrated in FIG. 4. Movement of the intraosseous access device into this configuration also advantageously locks the intraosseous access device in this configuration. Also advantageously, intraosseous access devices according to embodiments are single use devices that are fully disposable. Upon removing the pivot pin, the barrel and handle can be disposed of in separate waste flows. For example, the barrel can be disposed of in a sharps biohazard container and the handle, which can contain a power source, such as a battery, can be disposed of in appropriate facilities or recycled.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular arrangement of elements and steps disclosed herein have been selected by the inventors simply to describe and illustrate examples of the invention and are not intended to limit the scope of the invention or its protection, which is to be given the full breadth of the appended claims and any and all equivalents thereof.

What is claimed is:

1. An intraosseous access device, comprising:

a barrel having a closed end and an open end; a motor disposed within the barrel;

a slide carrier attached to the motor and configured to actuate throughout the barrel;

a rotating stylet assembly including a stylet, the rotating stylet assembly attached to and configured to be rotated by the motor, and configured to actuate with the motor throughout the barrel;

a handle attached to the barrel, the handle having a trigger configured to signal the motor; and a shield disposed within the barrel configured to move between an open state such that actuation of the rotating stylet assembly is permitted, and a closed state such that actuation of the rotating stylet assembly is inhibited;

wherein the stylet further comprises a tapered end; and wherein the shield further defines a shield aperture, the shield aperture having a diameter between the smallest diameter of the tapered end and the largest diameter of the tapered end.

2. The intraosseous access device of claim 1, wherein the shield further defines a lip, the lip inhibiting actuation of the stylet while the shield is in the closed state.

3. The intraosseous access device of claim 1, wherein the shield further defines a lip, the lip inhibiting actuation of the stylet while the shield is in the closed state.

4. The intraosseous access device of claim 1, further comprising a shield container, wherein the shield container defines a container aperture, the shield container being attached to the open end of the barrel, wherein the shield is pivotally disposed within the container aperture.

5. The intraosseous access device of claim 4, wherein the shield is configured to pivot from the open state to the closed state upon retraction of the rotating stylet assembly.

6. The intraosseous access device of claim 1, further comprising a battery housed within the handle, the battery being configured to power the motor.

7. The intraosseous access device of claim 1, wherein the handle is pivotally attached to the barrel.

8. The intraosseous access device of claim 7, wherein the handle is pivotally attached using a removable pivot body, wherein the pivot body is configured to be placed within the open end of the barrel and to close the open end of the barrel.

9. The intraosseous access device of claim 7, wherein the handle is configured to move from a disabled state in a first pivot position to an enabled state in a second pivot position.

10. The intraosseous access device of claim 9, wherein the handle further defines a ledge that covers the open end of the barrel and inhibits actuation of the rotating stylet assembly when the handle is in the first pivot position.

11. The intraosseous access device of claim 1, further comprising a spring disposed within the barrel, the spring being configured to retract the rotating stylet assembly.

12. The intraosseous access device of claim 11, further comprising a button assembly disposed upon the barrel, the button assembly configured to signal the spring to retract the rotating stylet assembly upon the actuation of the button assembly.

13. The intraosseous access device of claim 11, wherein the spring is configured to retract the rotating stylet assembly upon the actuation of the rotating stylet assembly reaching a predetermined threshold.

14. The intraosseous access device of claim 1, further comprising a slide channel defined by the barrel; and a slide interface both disposed within the slide channel and attached to the slide carrier, the slide interface being configured to allow manual actuation of the slide carrier throughout the slide channel.

15. The intraosseous access device of claim 14, wherein the button assembly is both disposed adjacent to the slide interface and attached to the slide carrier, such that the button assembly is actuated along with the actuation of the slide carrier.

16. An intraosseous access device, comprising:

a barrel having a closed end and an open end;

a motor disposed within the barrel;

a slide carrier attached to the motor and configured to actuate throughout the barrel;

a rotating stylet assembly including a stylet having a tapered end, the rotating stylet assembly attached to and configured to be rotated by the motor, and configured to actuate with the motor throughout the barrel;

a handle attached to the barrel, the handle having a trigger configured to signal the motor and a battery housed within the handle, the battery being configured to power the motor; and a shield disposed within the barrel configured to move between an open state such that actuation of the rotating stylet assembly is permitted, and a closed state such that actuation of the rotating stylet assembly is inhibited, the shield including a shield aperture and a lip, the shield aperture having a diameter between the smallest diameter of the tapered end and the largest diameter of the tapered end, the lip inhibiting actuation of the stylet while the shield is in the closed state.

17. The intraosseous access device of claim 16, wherein the handle is pivotally attached to the barrel using a removable pivot body, wherein the pivot body is configured to be placed within the open end of the barrel and to close the open end of the barrel.

18. The intraosseous access device of claim 17, wherein the handle is configured to move from a disabled state in a first pivot position to an enabled state in a second pivot position.

19. An intraosseous access device, comprising:

a barrel having a closed end and an open end;

a motor disposed within the barrel;

a slide carrier attached to the motor and configured to actuate throughout the barrel;

a slide channel defined by the barrel;

a slide interface both disposed within the slide channel and attached to the slide carrier, the slide interface being configured to allow manual actuation of the slide carrier throughout the slide channel;

a rotating stylet assembly including a stylet having a tapered end, the rotating stylet assembly attached to and configured to be rotated by the motor, and configured to actuate with the motor throughout the barrel;

a button assembly is both disposed adjacent to the slide interface and attached to the slide carrier, such that the button assembly is actuated along with the actuation of the slide carrier;

a spring disposed within the barrel, the spring being configured to retract the rotating stylet assembly;

a handle attached to the barrel, the handle having a trigger configured to signal the motor and a battery housed within the handle, the battery being configured to power the motor; and a shield disposed within the barrel configured to move between an open state such that actuation of the rotating stylet assembly is permitted, and a closed state such that actuation of the rotating stylet assembly is inhibited, the shield including a shield aperture and a lip, the shield aperture having a diameter between the smallest diameter of the tapered end and the largest diameter of the tapered end, the lip inhibiting actuation of the stylet while the shield is in the closed state.

* * * * *